(12) United States Patent
Payne et al.

(10) Patent No.: US 10,245,117 B2
(45) Date of Patent: *Apr. 2, 2019

(54) TISSUE EXPANDERS, IMPLANTS, AND METHODS OF USE

(71) Applicant: AirXpanders, Inc., San Jose, CA (US)

(72) Inventors: F. Mark Payne, Palo Alto, CA (US); Ryan S. Han, Saratoga, CA (US); Jacob Jay Rice, Sunnyvale, CA (US); Eadon Jacobs, Mountain View, CA (US); Scott Allen Dodson, Morgan Hill, CA (US)

(73) Assignee: AirXpanders, Inc., San Jose, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 15/389,222

(22) Filed: Dec. 22, 2016

(65) Prior Publication Data

US 2017/0165025 A1    Jun. 15, 2017

Related U.S. Application Data

(63) Continuation of application No. 14/186,985, filed on Feb. 21, 2014, now Pat. No. 9,526,584.

(60) Provisional application No. 61/767,754, filed on Feb. 21, 2013, provisional application No. 61/767,758, filed on Feb. 21, 2013.

(51) Int. Cl.
| | |
|---|---|
| *A61F 2/12* | (2006.01) |
| *A61B 19/00* | (2006.01) |
| *A61B 90/00* | (2016.01) |
| *A61B 17/00* | (2006.01) |

(52) U.S. Cl.
CPC ............... *A61B 90/02* (2016.02); *A61F 2/12* (2013.01); *A61B 2017/00212* (2013.01); *A61B 2017/00221* (2013.01); *A61B 2017/00792* (2013.01); *A61F 2210/0076* (2013.01); *A61F 2250/0002* (2013.01); *A61F 2250/0003* (2013.01); *A61F 2250/0004* (2013.01)

(58) Field of Classification Search
CPC .......................................................... A61F 2/12
USPC ......................................................... 623/7–8
See application file for complete search history.

(56) References Cited

U.S. PATENT DOCUMENTS

| | | | |
|---|---|---|---|
| 3,174,455 A | 3/1965 | Peterson | |
| 3,600,718 A | 8/1971 | Boone | |
| 3,706,462 A | 12/1972 | Lilly | |
| 3,841,654 A | 10/1974 | Lewis | |
| 3,852,833 A | 12/1974 | Koneke et al. | |
| 3,934,274 A | 1/1976 | Hartley, Jr. | |
| 4,217,889 A | 8/1980 | Radovan et al. | |

(Continued)

FOREIGN PATENT DOCUMENTS

| | | |
|---|---|---|
| EP | 0197726 B1 | 1/1992 |
| EP | 0469165 A1 | 2/1992 |

(Continued)

OTHER PUBLICATIONS

Adler et al.; Tissue Expander Infections in Pediatric Patients; Plast Reconstr Surg; vol. 125; No. 2; pp. 484-489; Aug. 2009.

(Continued)

*Primary Examiner* — Suzette J Gherbi
(74) *Attorney, Agent, or Firm* — Shay Glenn LLP

(57) ABSTRACT

Tissue expanders and methods of use. In some embodiments the tissue expanders are adapted to reduce wear on one or more components.

44 Claims, 10 Drawing Sheets

(56) References Cited

U.S. PATENT DOCUMENTS

| | | | |
|---|---|---|---|
| 4,264,990 A | 5/1981 | Hamas | |
| 4,550,720 A | 11/1985 | Trick | |
| 4,574,780 A | 3/1986 | Manders | |
| 4,615,704 A | 10/1986 | Frisch | |
| 4,643,733 A | 2/1987 | Becker | |
| 4,651,717 A | 3/1987 | Jakubczak | |
| 4,666,447 A | 5/1987 | Smith et al. | |
| 4,671,255 A | 6/1987 | Dubrul et al. | |
| 4,773,908 A | 9/1988 | Becker | |
| 4,841,992 A | 6/1989 | Sasaki et al. | |
| 4,899,764 A | 2/1990 | Gauger | |
| 4,950,292 A | 8/1990 | Audretsch | |
| 4,952,419 A | 8/1990 | De Leon et al. | |
| 4,955,905 A | 9/1990 | Reed | |
| 4,969,899 A | 11/1990 | Cox, Jr. | |
| 5,005,591 A | 4/1991 | Austad | |
| 5,049,106 A | 9/1991 | Kim et al. | |
| 5,068,225 A | 11/1991 | Pennell et al. | |
| 5,092,348 A | 3/1992 | Dubrul et al. | |
| 5,109,875 A | 5/1992 | Gottlieb | |
| 5,129,915 A | 7/1992 | Cantenys | |
| 5,133,753 A | 7/1992 | Bark et al. | |
| 5,141,508 A | 8/1992 | Bark et al. | |
| 5,146,933 A | 9/1992 | Boyd | |
| 5,236,454 A | 8/1993 | Miller | |
| 5,318,533 A | 6/1994 | Adams et al. | |
| 5,358,521 A | 10/1994 | Shane | |
| 5,376,117 A | 12/1994 | Pinchuk et al. | |
| 5,383,929 A | 1/1995 | Ledergerber | |
| 5,480,430 A | 1/1996 | Carlisle et al. | |
| 5,496,368 A | 3/1996 | Wiese | |
| 5,525,275 A | 6/1996 | Iversen et al. | |
| 5,571,178 A | 11/1996 | Ledergerber | |
| 5,571,179 A | 11/1996 | Manders et al. | |
| 5,653,726 A | 8/1997 | Kieturakis | |
| 5,658,330 A | 8/1997 | Carlisle et al. | |
| 5,720,762 A | 2/1998 | Bass | |
| 5,728,064 A | 3/1998 | Burns et al. | |
| 5,776,159 A | 7/1998 | Young | |
| 5,817,325 A | 10/1998 | Sawan et al. | |
| 5,849,311 A | 12/1998 | Sawan et al. | |
| 5,855,588 A | 1/1999 | Young | |
| 5,869,073 A | 2/1999 | Sawan et al. | |
| 5,938,669 A | 8/1999 | Klaiber et al. | |
| 5,964,803 A | 10/1999 | Iversen et al. | |
| 5,984,942 A | 11/1999 | Alden et al. | |
| 6,030,632 A | 2/2000 | Sawan et al. | |
| 6,055,989 A | 5/2000 | Rehnke | |
| 6,062,596 A | 5/2000 | Boydston et al. | |
| 6,071,309 A | 6/2000 | Knowlton | |
| 6,126,931 A | 10/2000 | Sawan et al. | |
| 6,180,584 B1 | 1/2001 | Sawan et al. | |
| 6,187,043 B1 | 2/2001 | Ledergerber | |
| 6,203,570 B1 | 3/2001 | Baeke | |
| 6,264,936 B1 | 7/2001 | Sawan et al. | |
| 6,494,879 B2 | 12/2002 | Lennox et al. | |
| 6,562,056 B2 | 5/2003 | Jervis | |
| 6,579,301 B1 | 6/2003 | Bales et al. | |
| 6,645,225 B1 | 11/2003 | Atkinson | |
| 6,668,836 B1 | 12/2003 | Greenburg et al. | |
| 6,755,861 B2* | 6/2004 | Nakao | A61F 2/12 623/7 |
| 6,953,429 B2 | 10/2005 | Forsell | |
| 7,033,373 B2 | 4/2006 | de la Torre et al. | |
| 7,144,407 B1 | 12/2006 | Lasersohn | |
| 7,575,596 B2 | 8/2009 | Bowman et al. | |
| 7,762,982 B1 | 7/2010 | Shah | |
| 8,180,438 B2* | 5/2012 | Brockway | A61N 1/0504 600/378 |
| 8,394,118 B2* | 3/2013 | Jones | A61F 2/12 606/192 |
| 8,617,198 B2* | 12/2013 | Jones | A61F 2/12 606/192 |
| 8,808,322 B2* | 8/2014 | Jones | A61F 2/12 606/192 |
| 9,526,584 B2* | 12/2016 | Payne | A61B 90/02 |
| 2001/0004709 A1 | 6/2001 | Dubrul | |
| 2003/0074084 A1* | 4/2003 | Nakao | A61F 2/12 623/23.67 |
| 2004/0147953 A1* | 7/2004 | Gedebou | A61B 90/02 606/198 |
| 2005/0116798 A1 | 6/2005 | Bintoro et al. | |
| 2005/0267595 A1 | 12/2005 | Chen et al. | |
| 2006/0069403 A1* | 3/2006 | Shalon | A61F 2/12 606/192 |
| 2006/0079727 A1 | 4/2006 | Chernomorsky et al. | |
| 2006/0111777 A1 | 5/2006 | Chen | |
| 2006/0155261 A1 | 7/2006 | Bek et al. | |
| 2006/0235482 A1 | 10/2006 | Forsell | |
| 2007/0032819 A1 | 2/2007 | McEwen et al. | |
| 2007/0197963 A1 | 8/2007 | Griffiths et al. | |
| 2007/0233273 A1 | 10/2007 | Connell | |
| 2008/0221704 A1 | 9/2008 | Aray | |
| 2009/0210056 A1 | 8/2009 | Forsell | |
| 2010/0010531 A1 | 1/2010 | Shalon et al. | |
| 2011/0152913 A1 | 6/2011 | Jones et al. | |
| 2012/0022540 A1 | 1/2012 | Chasmawala et al. | |
| 2012/0078366 A1* | 3/2012 | Jones | A61F 2/12 623/8 |
| 2013/0231743 A1* | 9/2013 | Becker | A61F 2/12 623/8 |
| 2013/0245758 A1* | 9/2013 | Chitre | A61M 39/0208 623/8 |

FOREIGN PATENT DOCUMENTS

| | | |
|---|---|---|
| EP | 0338701 B1 | 6/1992 |
| EP | 2453840 B1 | 2/2016 |
| FR | 2615397 A1 | 11/1988 |
| JP | 61234852 A | 10/1986 |
| JP | 08173542 A | 7/1996 |
| WO | WO80/00302 A1 | 3/1980 |
| WO | WO95/03752 A1 | 2/1995 |
| WO | WO97/27829 A1 | 8/1997 |
| WO | WO98/50100 A1 | 11/1998 |
| WO | WO00/19914 A1 | 4/2000 |
| WO | WO01/19283 A2 | 3/2001 |
| WO | WO01/47441 A2 | 7/2001 |
| WO | WO03/001966 A2 | 1/2003 |
| WO | WO2004/043303 A2 | 5/2004 |
| WO | WO2004/066812 A2 | 8/2004 |

OTHER PUBLICATIONS

Antony et al.; Acellular human dermis implantation in 153 immediate two-stage tissue expander breast reconstructions . . . ; Plast Reconstr Surg; vol. 125; No. 6; pp. 1606-1614; Jun. 2010.

Antony et al.; Salvage of tissue expander in the setting of mastectomy flap necrosis . . . ; Plast Recontr Surg; vol. 124; No. 2; pp. 356-363; Aug. 2009.

Argenta; Reconstruction of the Breast by Tissue Expansion; Clinic Plastic Surg; vol. 11; No. 2; pp. 257-264; Apr. 1984.

Armstrong et al.; Infection Following Breast Reconstruction; Ann Plast Surg; vol. 23; No. 4; pp. 284-288; Oct. 1989.

Austad; Evolution of the Concept of Tissue Expansion; Facial Plastic Surg; vol. 5; No. 4; pp. 277-279; Jul. 1988.

Beasley; Discussion: Eighty-four consecutive breast reconstructions using a textured silicone tissue expander (Maxwell); Plast Reconstr Surg; vol. 89; pp. 1035-1036; Jun. 1992.

Becker et al.; AlloDerm v DermaMatrix in immediate expander-based breast reconstruction . . . ; Plast Reconstr Surg; vol. 123; No. 1; pp. 1-6; Jan. 2009.

Bennett et al.; The History of Tissue Expansion; J Dermatol Surg Oncol; vol. 19; pp. 1066-1073; Dec. 1993.

Berge et al.; Tissue Expansion Using Osmotically Active Hydrogel Systems . . . ; Plast Reconstr Surg; vol. 108; No. 1; pp. 1-5; Jul. 2001.

Borba et al.; Self-inflating system of tissue expansion using gas (experimental study); Rev. Soc. Bras. Cir. Plast. Esthet. Reconstr.;

(56) References Cited

OTHER PUBLICATIONS vol. 9; pp. 70-78; 1993 (year of pub. sufficiently earlier than effective US filing date and any foreign priority date).
Brandi et al.; Carbon Dioxide Therapy: effects on skin irregularity and its use as a complement to liposuction; Aesth. Plast. Surg.; vol. 28; pp. 222R225; Jul.-Aug. 2004.
Buck et al.; Accellular dermis-assisted breast reconstruction with the use of crescentric tissue expansion . . . ; Aesthet Surg J; vol. 30; No. 2; pp. 194-200; Mar. 2010.
Camilleri et al.; A review of 120 Becker permanent tissue expanders in reconstruction of the breast; Br J Plastic Surg; vol. 49; pp. 346-351; Sep. 1996.
Chawla et al.; Radiotherapy and breast reconstruction: complications and cosmesis with tram versus tissue expander/implant; Int Jrnl Rad Onc Bio Phy; vol. 54; No. 2; pp. 520-526; Oct. 2002.
Chew et al.; Becker expander implants: truly a long term single stage reconstruction?; J Plastic Recontr & Aesthet Surg; vo. 63; pp. 1300-1304; Aug. 2010.
Christante et al.; Using complications associated with postmastectomy radiation and immediate breast reconstruction to improve surgical decision making; Arch Surg; vol. 145; No. 9; pp. 873-878; Sep. 2010.
Chun et al.; Implant-based breast reconstruction using acellular dermal matrix and the risk of postoperative complications; Plast Recontr Surg; vol. 125; No. 2; pp. 429-436; Feb. 2010.
Cohen et al.; Analysis of risks and aesthetics in a consecutive series of tissue expansion breast reconstructions; Plast Reconstr Surg; vol. 89; No. 5; pp. 840-843; May 1992.
Collis et al.; Breast reconstruction by tissue expansion . . . ; Br J Plastic Surg; vol. 53; pp. 37-41; Jan. 2000.
Cordeiro et al.; A single surgeon's 12-year experience with tissue expander/implant breast reconstruction . . . ; Plast Recontr Surg; vol. 118; No. 4; pp. 832-839; Sep. 15, 2006.
Dickson et al.; The complications of tissue expansion in breast reconstruction: a review of 75 cases; Br J Plast Surg; vol. 40; pp. 629-635; Nov. 1987.
Disa et al.; The Premature Removal of Tissue Expanders in Breast Reconstruction; Plast Reconstr Surg; vol. 104; No. 6; pp. 1662-1665; Nov. 1999.
Edlich et al.; Advances in Breast Reconstruction After Mastectomy; J Long Term Eff Med Implants; vol. 15; No. 2; pp. 197-207; 2005 (year of pub. sufficiently earlier than effective US filing date and any foreign priority date).
Francis et al.; Independent Risk Factors for Infection in Tissue Expander Breast Reconstruction; Plast Reconstr Surg; vol. 124; No. 6; pp. 1790-1796; Dec. 2009.
Frankhouse et al.; Carbon Dioxide/Digital Subtraction Arteriography-Assisted Transluminal Angioplasty; Ann Vasc Surg; vol. 9; No. 5; pp. 448-452; Sep. 1995.
Gibney; The Long-Term Results of Tissue Expansion for Breast Reconstruction; Clinic Plastic Surg; vol. 14; No. 3; pp. 509-518; Jul. 1987.
Gibney; Use of a Permanent Tissue Expander for Breast Reconstruction; Plastic Reconstruct Surg; vol. 84; No. 4; pp. 607-617; Oct. 1989.
Gosain et al.; Pediatric tissue expansion for forehead reconstruction: A 13-year review and algorithm for its use (presentation abstract #13288 with photos); American Society of Plastic Surgeons; Plastic Surgery 2007; Baltimore, MD; 2 pgs.; Oct. 26-31, 2007.
Gosain et al.; Refinements of tissue expansion for pediatric forehead reconstruction: A 13-year experience; Plast. Reconstr. Surg.; 124(5); pp. 1559-1570; Nov. 2009.
Gui et al.; Immediate Breast Reconstruction Using Biodimensional Anatomical Permanent Expander Implants . . . ; Plast Reconstr Surg; vol. 111; No. 1; pp. 125-138; Jan. 2003.
Haddock et al.; Breast Reconstruction with Implants, Tissue Expanders and AlloDerm . . . ; Breast J; vol. 16; No. 1; pp. 14-19; Jan.-Feb. 2010.

Jhaveri et al.; Clinical Outcomes of Postmastectomy Radiation Therapy After Immediate Breast Reconstruction; J Radiat Oncol Biol Phys; vol. 72; No. 3; pp. 859-865; Nov. 2008.
Kronowitz; Delayed-Immediate Breast Reconstruction: Technical and Timing Considerations; Plast Recontr Surg; vol. 125; No. 2; pp. 463-474; Feb. 2010.
Krueger et al.; Complications and patient satisfaction following expander/implant breast reconstruction with and without radiotherapy; Int Jrnl Rad Onc Bio Phys; vol. 49; No. 3; pp. 713-721; Mar. 2001.
Lanier et al.; The Effect of Acellular Dermal Matrix Use on Complication Rates in Tissue Expander/Implant Breast Reconstruction; Ann Plast Surg; vol. 64; No. 5; pp. 674-678; May 2010.
Liu et al.; Does neoadjuvant chemotherapy for breast cancer increase complications during immediate breast reconstruction?; J Med Dent Sci; vol. 56; pp. 55-60; Mar. 2009.
Logan et al.; A Control Unit for Maximal Rate Continuous Tissue Expansion (CTE); Biomed Sci Instrum; vol. 25; pp. 27-33; Dec. 1988.
Losken et al.; Outcomes Evaluation Following Bilateral Breast Reconstruction Using Latissimus Dorsi Myocutaneous Flaps; Ann Plast Surg; vol. 65; No. 1; pp. 17-22; Jul. 2010.
Losken; Early Results Using Sterilized Acellular Human Dermis (NeoForm) in Postmastectomy Tissue Expander Breast Reconstruction; Plast Recontr Surg; vol. 123/ No. 6; pp. 1654-1658; Jun. 2009.
Machida et al.; Immediate v Chronic Tissue Expansion; Ann Plast Surg; vol. 26; No. 3; pp. 227-232; Mar. 1991.
Mahdi et al.; Expandable Anatomical Implants in Breast Reconstructions: A Prospective Study; Br J Plast Surg; vol. 51; pp. 425-430; Sep. 1998.
Marks; (Discussion) Comparison between rapid and slow tissue expansion in breast reconstruction; Plastic and Reconstructive Surgery; pp. 671-672; Apr. 1993.
Maxwell et al.; Eighty-four consecutive breast reconstructions using a textured silicone tissue expander; Plastic and Reconstructive Surgery; vol. 89; No. 6; pp. 1022-1034; Jun. 1992.
May et al.; Smooth vs textured expander implants: a double-blind study of capsule quality and discomfort in simultaneous bilateral breast reconstruction patients; Ann Plast Surg; vol. 32; No. 3; pp. 225-233; Mar. 1994.
McCarthy et al.; Predicting complications following expander/implant breast reconstruction: an outcomes analysis based on preoperative clinical risk; Plast Reconstr Surg; vol. 121; No, 6; pp. 1886-1892; Jun. 2008.
Mitchell; Carbon dioxide flooding the operative field to minimize or prevent air embolism during open heart operations; Textbook of Extracorporeal Technology; 6 pgs.; 2003; updated Jan. 2009.
Mitchem et al.; Impact of neoadjuvant chemotherapy on rate of tissue expander/implant loss and progression to successful breast reconstruction following mastectomy; Am J Surg; vol. 196; pp. 519-522; Oct. 2008.
Mohmand et al.; Home Inflation of Tissue Expanders: A Safe and Reliable Alternative; Br J of Plast Surg; vol. 54; pp. 610-614; Oct. 2001.
Nahabedian et al.; Infectious Complications Following Breast Reconstruction with Expanders and Implants; Plast Reconstr Surg; vol. 112; No. 2; pp. 467-476; Aug. 2003.
Namnoum; Expander/Implant Reconstruction with AlloDerm: Recent Experience; Plast Reconstr Surg; vol. 124; No. 2; pp. 387-394; Aug. 2009.
Neumann; The expansion of an area of skin by progressive distention of a subcutaneous balloon; Plastic & Reconstructive Surgery; 19(2); pp. 124-130; Feb. 1957.
Nordstrom; Tissue Expansion; Butterworth-Heinemann (publishers); Chapters 8, 18, & 19; 2004 (year of pub. sufficiently earlier than effective US filing date and any foreign priority date).
Nunes et al.; Continuous expansion for the treatment of skin deformities; Aesth. Plast. Surg.; vol. 20; pp. 347-349; Jul./Aug. 1996.
Pusic et al.; An accelerated approach to tissue expansion for breast reconstruction: experience with intraoperative and rapid postoperative expansion in 370 reconstructions; Plastic and Reconstructive Surgery; vol. 3; No. 6; pp. 1871-1875; May 2003.

(56) References Cited

OTHER PUBLICATIONS

Pusic et al.; Clinical research in breast surgery: reduction and postmastectomy reconstruction; Clin Plas Surg; vol. 35; pp. 215-226; Apr. 2008.
Radovan; Breast reconstruction after mastectomy using the temporary expander; Plas Reconstr Surg; vol. 69; No. 2; pp. 195-206; Feb. 1982.
Revis; Tissue Expansion; emedicine (from WebMD); 14 pgs.; Oct. 2005.
Ronert et al.; The beginning of a new era in tissue expansion: self-filling osmotic tissue expander—four-year clinical experience; Plastic and Reconstructive Surgery; vol. 114; No. 5; pp. 1025-1031; Oct. 2004.
Saint-Cyr et al.; Use of the Serratus Anterior Fascia Flap for Expander Coverage in Breast Reconstruction; Plast Reconstr Surg; vol. 125; No. 4; pp. 1057-1064; Apr. 2010.
Sasaki; Interoperative Sustained Limited Expansion (ISLE) as an Immediate Reconstructive Technique; Clinic Plastic Surg; vol. 14; No. 3; pp. 563-573; Jul. 1987.
Sasaki; Intraoperative Expansion as an Immediate Reconstructive Technique; Facial Plastic Surg; vol. 5; No. 4; pp. 362-378; Jul. 1988.
Sasaki; Tissue Expansion in Reconstructive and Aesthetic Surgery; Mosby (publishers); pp. 190-192 and 206-242; Jun. 1998.
Sbitany et al.; Acellular Dermis-Assisted Prosthetic Breast Reconstruction versus Complete Submuscular Coverage: A Head-to-Head Comparison of Outcomes; Plast Reconstr Surg; vol. 124; No. 6; pp. 1735-1740; Dec. 2009.
Schmidt et al.; Continuous versus conventional tissue expansion: experimental verification of a new technique; Plast Reconstr Surg; vol. 87; No. 1; pp. 10-15; Jan. 1991.
Slavin et al.; Sixty consecutive breast reconstructions with the inflatable expander: a critical appraisal; Plast Reconstr Surg; vol. 86; No. 5; pp. 910-919; Nov. 1990.
Spear et al.; A retrospective analysis of outcomes using three common methods for immediate breast reconstruction; Plas Reconstr Surg; vol. 122; No. 2; pp. 340-347; Aug. 2008.
Spear et al.; Acellular Dermis-Assisted Breast Reconstruction; Aesthetic Plast Surg; vol. 32; pp. 418-425; May 2008.
Spear et al.; Breast Reconstruction with Implants and Expanders; Plas Reconstr Surg; vol. 107; No. 1; pp. 177-187; Jan. 2001.
Spear et al.; Immediate breast reconstruction in two stages using textured, integrated-valve tissue expanders and breast implants . . . ; Plast Reconstr Surg; vol. 101; No. 1; pp. 53-63; Jan. 1998.
Spear et al.; Prophylactic mastectomy and reconstruction: clinical outcomes and patient satisfaction; Plas Reconstr Surg; vol. 122; No. 1; pp. 1-9; Jul. 2008.
Spear et al.; Prophylactic Mastectomy: Indications, Options, and Reconstructive Alternatives; Plast Reconstr Surg; vol. 115; No. 3; pp. 891-909; Mar. 2005.
Strock; Two-Stage Expander Implant Reconstruction: Recent Experience; Plast Reconstr Surg; col. 124; No. 5; pp. 1429-1436; Nov. 2009.
Sullivan et al.; True Incidence of All Complications following Immediate and Delayed Breast Reconstruction; Plas Reconstr Surg; vol. 122; No. 1; pp. 19-28; Jul. 2008.
Swart et al.; Breast Cancer; eMedicine; 54 pgs.; Dec. 17, 2010.
Tassan et al.; Tissue Expansion; Safr Med J; vol. 71; pp. 703-706; Jun. 6, 1987.
Tepper et al.; Three-dimensional imaging provides valuable clinical data to aid in unilateral tissue expander-implant breast reconstruction; Breast J; vol. 14; No. 6; pp. 543-550; Nov.-Dec. 2008.
Toranto et al.; Endoscopic versus open tissue-expander placement: is less invasive better?; Plast Reconstr Surg; vol. 119; No. 3; pp. 894-906; Mar. 2007.
Trabulsy et al.; Changing trends in postmastectomy breast reconstruction: a 13-year experience; Plast Reconstr Surg; vol. 93; No. 7; pp. 1418-1427; Jun. 1994.
Wickman; Comparison between rapid and slow tissue expansion in breast reconstruction; Plastic and Reconstructive Surgery; 91(4); pp. 663-670; Apr. 1993.
Widgerow et al.; Patient-controlled expansion: applying a new technique to breast reconstruction; Aesth. Plast. Surg.; vol. 31; pp. 299-305; May-Jun. 2007.
Woods et al.; Breast reconstruction with tissue expanders: obtaining an optimal result; Ann Plast Surg; vol. 28; pp. 390-396; Apr. 1992.
Yanko-Arzi et al.; Breast Reconstruction: Complication Rate and Tissue Expander Type; Aesthetic Plast Surg; vol. 33; pp. 489-496; Jul. 2009.
Youm et al.; Complications of tissue expansion in a public hospital; Ann Plast Surg; vol. 42; pp. 396-402; Apr. 1999.
Jones et al.; U.S. Appl. No. 15/368,475 entitled "Tissue expanders and methods of use," filed Dec. 2, 2016.

\* cited by examiner

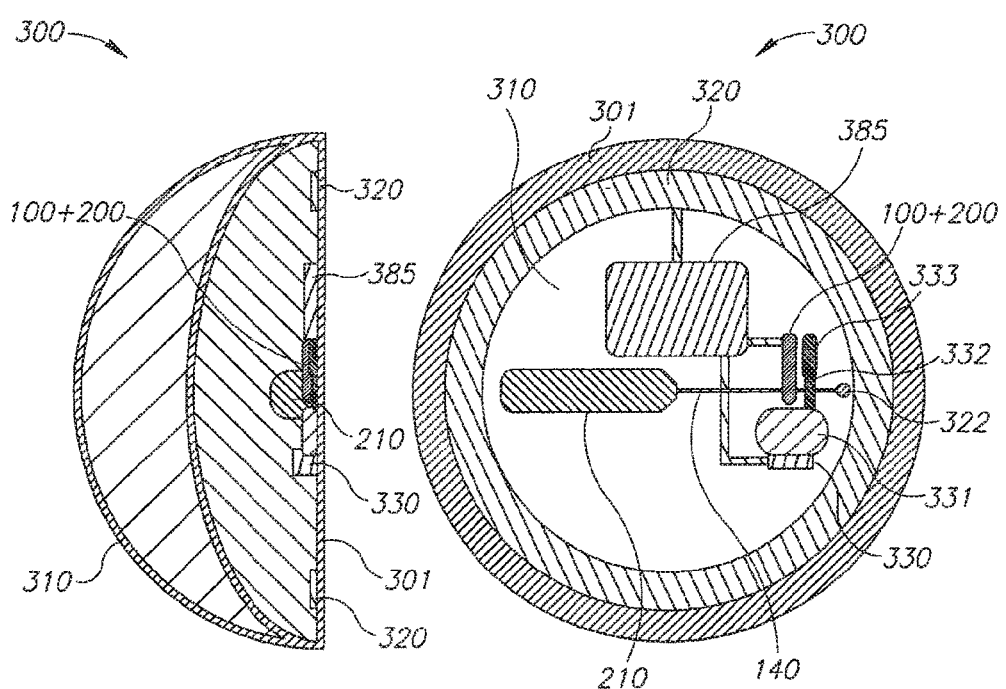
FIG. 1B  FIG. 1C

TISSUE EXPANDERS, IMPLANTS, AND METHODS OF USE

CROSS REFERENCE TO RELATED APPLICATIONS

This application is a continuation of U.S. application Ser. No. 14/186,985, filed Feb. 21, 2014, now U.S. Pat. No. 9,526,584, which application claims the priority of U.S. Prov. App. 61/767,754, filed Feb. 21, 2013 and U.S. Prov. App. 61/767,758, filed Feb. 21, 2013, the disclosures of which are incorporated herein by reference.

This application is related to and incorporates herein by reference the disclosures of the following applications: U.S. Pub. No. 2011/0152913, published Jun. 23, 2011; U.S. Prov. App. No. 61/288,197, filed Dec. 18, 2009; U.S. Pub. No. 2006/0069403, published Mar. 30, 2006; U.S. Prov. App. No. 60/612,018, filed Sep. 21, 2004; and U.S. Prov. App. No. 60/688,964, filed Jun. 9, 2005.

INCORPORATION BY REFERENCE

All publications and patent applications mentioned in this specification are herein incorporated by reference to the same extent as if each individual publication or patent application was specifically and individually indicated to be incorporated by reference.

BACKGROUND

A deficit of normal tissue in a subject may result from, for example, burns, tumor resection surgery (e.g., mastectomy), or congenital deformities. Often, the tissue in deficit is skin and/or underlying connective tissue. The tissue in deficit can also be an intrabody duct (e.g., urethras or GI tract).

One method of correcting skin deficit is to stimulate creation of new skin. Implantation of a device that expands and stretches the existing skin causes a growth response in which new skin is created.

The first report of tissue expansion was in 1956 by Charles Neumann (Plastic & Reconstructive Surgery; Vol 19 (2); 124-130) who implanted a rubber balloon attached to a percutaneous tube to enable intermittent expansion for the purpose of reconstructing a partially amputated ear. Since that time, the idea of tissue expansion devices has undergone commercial development.

Most commercially available tissue expanders function as an implantable balloon with an extracorporeal or imbedded valve that allows periodic inflation. Typically, it is a doctor that performs the inflation. Since the inflation events are relatively infrequent, a significant inflation pressure is typically applied at each doctor's visit in order to achieve maximum effect from each visit. As a result of this inflation pressure during a clinic visit, a relatively sudden tissue stretch occurs. This may cause subjects to suffer discomfort and/or tissue ischemia. The relatively large inflation pressure can also adversely affect underlying structures (e.g., cause concavities in underlying bone). In addition, high pressure may create restrictive capsules around the implant and/or cause tissue failure. Some previously available alternatives used a needle for inflation or filling, creating a potential source of infection.

In order to overcome such issues, continuously expanding devices have been developed. For example, osmotic expanders have been reported by Austad in 1979, Berge in 1999, and Olbrisch in 2003 (see U.S. Pat. Nos. 5,005,591 and 5,496,368). A commercial version is available from Osmed Corp. in a limited range of sizes. These devices use a polymeric osmotic driver to expand a silicone implant by absorbing interstitial fluid (ISF). A potential problem of such devices is the lack of control or adjustability after implantation with respect to expansion variables such as pressure, volume, onset of expansion, and end of expansion once they have been deployed.

U.S. Pat. No. 6,668,836 to Greenberg et al. describes a method for pulsatile expansion of tissue using an external hydraulic pump. The external hydraulic pump is bulky and may lead to negative subject reactions. The percutaneous attachment reduces subject mobility and may be a source of contamination. U.S. Pat. No. 4,955,905 to Reed teaches an external monitor for pressure of an implanted fluid filled tissue expansion device. U.S. Pat. Nos. 5,092,348 and 5,525,275 to Dubrul and Iverson respectively teach implantable devices with textured surfaces. U.S. Patent Publication No. 2004/0147953 by Gebedou teaches a device which relies upon an internal mechanical force as a means of avoiding use of fluids for tissue expansion. U.S. Pat. Nos. 6,264,936; 6,180,584; 6,126,931; 6,030,632; 5,869,073; 5,849,311 and 5,817,325 deal generally with the concept of antimicrobial coatings.

The disclosure herein describes tissue expanders and methods of use that overcome shortcomings of existing tissue expanders.

SUMMARY OF THE DISCLOSURE

One aspect of the disclosure is a tissue expander comprising an implantable portion comprising a fluid source in communication with an expandable chamber, a first deformable member, a second deformable member, and a lubricious material disposed between the first and second deformable members to reduce friction between the first and second deformable members.

In some embodiments the first deformable member at least partially defines the expandable chamber. The second member can be disposed outside of the expandable chamber. The second deformable member can be configured as a barrier layer to the fluid and is disposed outside of the expandable chamber.

In some embodiments the tissue expander further comprises an outer shell disposed at least partially around the first and second deformable members. The outer shell can be an elastic shell.

In some embodiments the first and/or second deformable members have pre-formed configurations, and either can include an inelastic material with the pre-formed configuration. The first and second deformable members can have pre-formed configurations that are substantially the same.

In some embodiments the first and second deformable members are thin-walled deformable members. The first deformable member can be disposed inside the second deformable member, and the first deformable member can have a thickness between about 75 microns and about 150 microns. The second deformable member can have a thickness between about 25 microns and about 75 microns. The first deformable member can be disposed inside the second deformable member, and the second deformable member can have a thickness between about 25 microns and about 75 microns. The first deformable member can be disposed inside the second deformable member, and the first deformable member can have a thickness that is about 1.5 to about 8 times the thickness of the second deformable member.

In some embodiments at least one of the first and second deformable members comprises multiple layers of material secured together.

In some embodiments the lubricious material has a viscosity of at least 50 cP.

In some embodiments the lubricious material is a biocompatible lubricant, such as a silicone-based lubricant.

In some embodiments the first deformable members is attached directly to the second deformable member, and the first and second deformable members can be secured to each other at respective peripheries of the first and second deformable members.

In some embodiments the expandable chamber includes an anterior portion, wherein the anterior portion includes the first and second deformable members. The expandable chamber can include a posterior backing coupled to the first deformable member.

In some embodiments the first deformable member has a communication component secured to it, wherein the communication component is configured for wireless communication with an external controller.

In some embodiments the volume of lubricious material disposed between the first and second members is between about 0.5 mL and about 2.5 mL, and can be between about 0.5 mL and about 2.0 mL.

In some embodiments the tissue expander further comprises an external controller adapted to be in communication with the implantable portion to enable fluid to be released from the fluid source into the expandable chamber.

In some embodiments the lubricious material comprises a coating on at least one of the two members.

In some embodiments the lubricous material provides substantially no additional thickness to the implantable portion.

One aspect of the disclosure is a tissue expander comprising: an implantable portion including an expandable chamber in fluid communication with a fluid source; a first deformable member at least partially defining the expandable chamber and having a pre-formed configuration; a second deformable member disposed about the first deformable member; and an outer shell disposed about the first and second deformable members.

In some embodiments the second deformable member has a pre-formed configuration. The first and second pre-formed configurations can be substantially the same.

In some embodiments the first and second deformable members form at least part of a gas barrier layer of the implantable portion that is substantially impermeable to fluid in the fluid source.

In some embodiments the outer shell is an elastic shell.

In some embodiments the first and second deformable members are thin-walled deformable members.

In some embodiment the first deformable member is disposed inside the second deformable member, and the first deformable member has a thickness between about 75 microns and about 150 microns. The second deformable member can have a thickness between about 25 microns and about 75 microns.

In some embodiments the first deformable member is disposed inside the second deformable member, and the second deformable member has a thickness between about 25 microns and about 75 microns.

In some embodiments the first deformable member is disposed inside the second deformable member, and the first deformable member has a thickness that is about 1.5 to about 8 times the thickness of the second deformable member.

In some embodiments the first deformable member has a communication component secured to it, wherein the communication component is configured for wireless communication with an external controller.

One aspect of the disclosure is a tissue expander comprising: an implantable portion comprising a fluid source in fluid communication with an expandable chamber, a communication element secured to the expandable chamber and movable relative to the expandable chamber; and an external controller configured for wireless communication with the communication component to enable fluid to be released from the fluid source into the expandable chamber.

In some embodiments the communication element is an antenna.

In some embodiments the communication element is stiffer than the expandable chamber.

In some embodiments the expandable chamber has a thickness between about 50 microns and about 150 microns.

In some embodiments the communication element is disposed inside a pocket, and the pocket is attached to the expandable chamber. The communication element can be secured inside the pocket such that it floats inside the pocket. Two sides of the pocket can be attached together at a plurality of discrete locations with at least one unattached location between the two sides. The pocket can be attached to the expandable chamber at a plurality of discrete locations with at least one unattached location where the pocket is not attached to the expandable chamber. The pocket can be secured to the expandable chamber around a periphery of the pocket at at least three locations with unsecured locations where the pocket is not attached to the expandable chamber.

In some embodiments the communication element is secured to a first portion of the expandable chamber that, in a side view of an expanded configuration of the expandable chamber, is less curved than a second portion of the expandable chamber.

In some embodiments the expandable chamber comprises an inelastic material with a preformed expanded configuration, and the communication element is secured to the inelastic material such that it can move relative to the inelastic material.

One aspect of the disclosure is a device adapted to be implanted in the breast, comprising a deformable chamber with a gel disposed therein; a deformable member at least partially surrounding the deformable chamber; and a lubricious material disposed between and in contact with the deformable chamber and deformable member.

In some embodiments the deformable chamber and deformable member are comprised of an elastic material.

In some embodiments the volume of lubricious material is less than about 5 mL, less than about 4 mL, less than about 3 mL, less than about 2 mL, or less than about 1 mL.

In some embodiments the lubricious material comprises a coating on at least one of the deformable chamber and deformable member.

BRIEF DESCRIPTION OF THE DRAWINGS

FIGS. 1B and 1C illustrate an exemplary implantable portion of a tissue expander system.

DETAILED DESCRIPTION

Figure 1A:
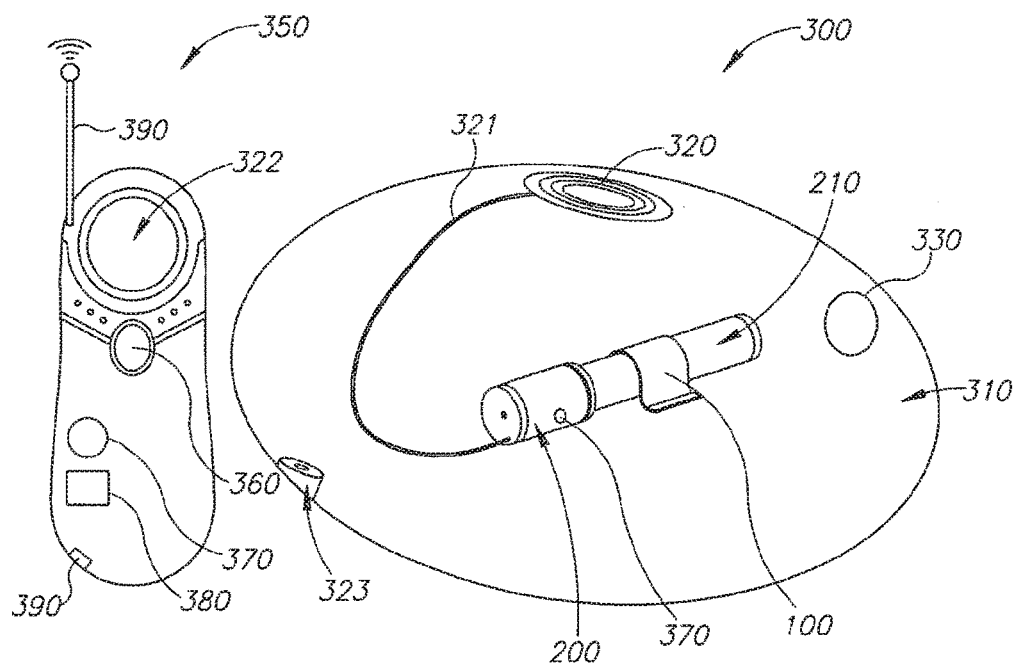
FIG. 1A illustrates an exemplary tissue expander system including a remote controller and an implantable portion.

The disclosure describes tissue expanders and methods of using them to expand tissue. In some embodiments of use the tissue expanders are used to expand tissue and create a "pocket" within tissue, into which a medical device, such as a permanent implant, may be positioned. For example without limitation, the tissue expanders can be used to create a pocket within breast tissue, into which a breast implant can be positioned after removal of the tissue expander. Additional exemplary uses are described in U.S. Prov. Appln. No. 61/767,758, filed Feb. 21, 2013, incorporated by reference herein.

FIGS. 1A-1D illustrate an exemplary tissue expander, exemplary details of which are also described in U.S. Pub. No. 2006/0069403, published Mar. 30, 2006. FIGS. 1A-1D illustrate a self-contained implantable tissue expansion device 300 that includes an expandable compartment 310. Device 300 includes a fill source, optionally a gas source 210. Device 300 is configured as a breast tissue expander positionable in a breast 610 of a subject. This may be undertaken, for example following surgery performed on breast (e.g., tumor resection). Optionally, device 300 expands over a period of time via transfer of gas from gas source 210 to expandable compartment 310. Device 300 can restore skin and/or muscle tissue of the breast to dimensions similar to those of a contra-lateral breast. Optionally, this facilitates implantation of a long term cosmetic implant in the breast so that the subject achieves approximate bilateral symmetry with the contra-lateral breast. Because gas can be packed under pressure in a small volume and later expand to a larger volume at a lower pressure, device 300 may be self-contained. Alternatively or additionally, a device that will eventually assume large proportions may be collapsed and implanted through a small incision.

In an exemplary embodiment, device 300 relies on a self-contained gas source 210. Optionally, source 210 contains a fixed amount of gas. Optionally, a fixed amount of gas makes unwanted over inflation less of a safety concern. In an exemplary embodiment of the invention, the fixed amount of gas in source 210 corresponds to a desired maximum inflation of expandable compartment 310. This makes explosion of compartment 310 as a result of sudden release of the contents of source 210 into compartment 310 unlikely.

Gas source 210 optionally has an internal volume of 1 cc to 50 cc, optionally 2 to 10 cc. In an exemplary embodiment of the invention, a compressed gas source 210 has a total internal volume of about 5 ml. Optionally a large tissue expansion may be achieved by providing 2.5 grams of $CO_2$ in a 5 ml internal-volume container. This provides about 1200 ml of $CO_2$ at 15 PSI (1 PSI above atmosphere at sea level). Alternatively or additionally, a 0.05 ml $CO_2$ source could provide a final volume of about 12 ml final volume. Optionally, many small gas sources 210 are provided in a single device 300.

In an additional exemplary embodiment device 300 includes an expandable compartment 310 adapted for implanting in a body of a subject and a gas source 210 coupled to said compartment; and at least one regulator adapted to be located within said body and selectively control gas flow from said source to said compartment. Optionally, source 210 is adapted to be external to a body of a subject and is connected by a tube to compartment 310.

The release of gas from source 210 can be controlled over a period of time. This contributes to a gradual inflation of compartment 310 which can reduce patient discomfort. Alternatively or additionally, more frequent and/or continuous expansion events may reduce the likelihood of the development of a restricting capsule. Small gradual expansion is hypothesized to result in less capsule formation, i.e., reduced capsule thickness, than expansion brought about by greater expansive force (pressure). In an exemplary embodiment, a treatment with device 300 according to the present invention might last 7 to 180 days, in some embodiments can be used in less than 1 month, and in some embodiments between two and three weeks. Actual treatment time might depend upon factors including, but not limited to, required degree of expansion and/or elasticity of tissue(s) to be expanded and/or growth characteristics of tissue to be expanded and/or subject compliance with treatment.

In an exemplary embodiment, additional control over transfer of gas from source 210 to compartment 310 is achieved by flow restriction. Device 300 optionally includes a valve, examples of which are described in U.S. Pub. No. 2011/0152913, published Jun. 23, 2011 and U.S. Pub. No. 2006/0069403, published Mar. 30, 2006. The valve may optionally regulate a flow of gas under pressure from gas source 210 into expandable compartment 310. An actuator may optionally apply additional regulation to valve 100. Exemplary actuators 200 are described in greater detail in U.S. Pub. No. 2006/0069403, published Mar. 30, 2006.

In an exemplary embodiment, a gradual expansion of tissue is desired. Optionally, gradual expansion indicates a period of several weeks, optionally several months, as much as six months or more. Optionally, a low rate of transfer of gas from gas source 210 to expandable compartment 310 is employed. Optionally, a valve is characterized by a low flow rate. Optionally, regulation of a flow rate through valve 100 is desired. Optionally, an actuator is included in device 300.

In an exemplary method of use, device 300 is employed as part of a method of repair after a tissue damage event has occurred. Tissue damage may be, for example, a tumor resection, such as a mastectomy. Optionally, modeling of the affected tissue is performed prior to tissue damage. Optionally, modeling of a matching contralateral tissue (e.g., breast) is performed. Device 300 is prepared optionally based on the modeling. Optionally, device 300 includes thermoplastic or thermosetting sections that are shaped during modeling. Optionally modeling includes calculation of a required incremental inflation volume and/or pressure that may be translated to an amount of a specific inflation gas in grams.

After preparation, device 300 is implanted. After implantation, device 300 expands over a period of time by transfer of gas from source 210 to compartment 310 causing tissue expansion. Optionally this process may be regulated or controlled as detailed herein. Once tissue expansion is complete, removal of device 300 may be performed, for example to implant a replacement long term implant. Optionally, device 300 is made permanent, for example by filling with a conventional implant material such as, for example, silicone gel or saline.

In another exemplary embodiment, tissue expansion device 300 is optionally employed to grow new skin to permit repair of damaged skin tissue at another location. Modeling is optionally not pursued in these uses because the device can disrupt a natural body contour as a means of creating excess skin for subsequent transfer. New skin may be induced to grow by increased tension resulting from expansion of the implanted device as described hereinabove. Optionally, the new skin is harvested and transferred to a new location as an autologous graft. In an exemplary embodiment of the invention, this strategy is employed to effect cosmetic repair. Optionally, the cosmetic repair may be for scar removal, to replace a tattooed area, to replace skin damaged by burns or to ameliorate pigment irregularities. Optionally, skin for transfer is created in a matching body area. For example, repair of a right side of the face might be pursued by implanting a device under the left cheek. Optionally, this might produce skin with similar characteristics to the damaged skin in terms of pigment and/or elasticity and/or hair prevalence and/or hair characteristics. According to these embodiments of the invention, a subject may voluntarily undergo a short term disfigurement in order to overcome long term tissue damage. In an exemplary embodiment of the invention, new skin is molded. Optionally, molding occurs during formation. Optionally, molding occurs during or after transplant. Optionally, molding is in conformation to a form attached to the device. Optionally, molding is in conformation to a form provided at a transplant site. In an exemplary embodiment of the invention, new skin grown in response to pressure provided by a device is employed to reconstruct an ear.

An inelastic shell may optionally include film laminates such as, for example, metalized Mylar (PET) (e.g., MC2-100; DuPont Teijin Films Hopewell, Va., USA) or metallized nylon or other metallized polymer films that may act as gas diffusion barriers, or a laminate of polypropylene, polyethylene or nylon as an outer skin with an inner gas barrier of poly(vinylidene chloride) and a polyethylene inner layer used for thermally bonding the film made by Dow Chemical Co. (for example, XUR-1689, Midland, Mich., USA) are suitable for use in the invention. In an exemplary embodiment of the invention, the inelastic shell is shaped by folding, optionally pleating or accordion folding.

Optionally, the inelastic shell is installed inside the elastic balloon so that accordion like unfolding of the inner shell is less apparent from outside. Optionally, one layer controls gas diffusion and/or imparts a desired shape. Optionally, one layer regulates expansion by providing a resistive force.

Optionally, the expandable compartment provides a natural body contour and/or natural feel. This may be accomplished, for example, by using a target tissue to model the compartment. For example, a breast prior to tumor resection, and/or a contralateral breast might be measured and/or cast to provide appropriate dimensions and/or aspect rations for the implantable portion of the tissue expander.

Alternatively or additionally, an inelastic shell may provide puncture and/or leak protection.

Optionally, total gas leakage from the expandable compartment is less than 5 ml/day, optionally less than 1 ml/day optionally about 0.11 ml/day. In an exemplary embodiment of the invention, the gas is selected to provide a desired leakage rate in combination with materials used to construct the expandable compartment. Desired rates may be achieved, for example, with film laminates as described hereinabove. Sealing of a Mylar shell of this type may be accomplished, for example, by application of heat and pressure using a commercially available heat sealer such as the one suitable for tray sealing for medical device packaging. For example, a 5 mm seal may be created by applying a 150 degree centigrade heating element with a pressure of 40 PSI for 1 second. For industrial production, heating elements may be specially shaped to produce implants with desired configurations. Additionally seals may be prepared by the use of an appropriate adhesive to allow for bonding of the sheets. Alternatively or additionally, inelastic sheets of different sizes and/or shapes may be bonded together to pre-form the implantable device. Optionally, a desired leakage rate is achieved by device by construction using materials with known leakage or permeation characteristics. This may be accomplished, for example, by employing materials with desired permeability and/or diffusion characteristics in construction of the expandable compartment. In an exemplary embodiment of the invention, carbon dioxide is employed for inflation of the expandable compartment and small amounts of excess gas may be safely vented from compartment within the body.

In an exemplary embodiment of the invention, a desired size and conformation of device 300 after expansion is known in advance. Because the total desired inflation volume of expandable compartment 310 is known, source 210 of device 300 configured to provide the desired volume by controlling an amount of gas loaded therein. Gas source 210 may be filled, for example, by using carbon dioxide at 800 PSI (room temperature) flowing through a 2 micron particulate filter into capillary tube 140 surrounded by PEEK tube 142. Source 210 is purged twice with pressurized gas and placed in an ice bath. Carbon dioxide gas condenses into source 210 at a rate of about 0.02 g/s so that a 2.5 gram charge of $CO_2$ may be achieved in just over 4 minutes. The exact amount of charge may optionally be determined by monitoring the extra weight of source 210. Once source 210 is filled, valve 100 may be attached. Attachment may be, for example, vial mated sets of threads on source 210 and valve 100. Optionally, a low loss "normally closed" valve 100 is employed and source 210 may be filled days, or even weeks, before deployment in the device. Optionally, an additional seal is employed to reduce gas loss through the valve during storage. Optionally, sources 210 with desired increments of gas fill are prepared commercially and supplied as components for installation in the device.

Optionally, compartment 310 leaks at a known rate. This means that if inflation is carried out to the point of discomfort, gradual relief will occur without any active intervention. Alternatively or additionally, a pressure sensitive valve releases excess pressure from compartment 310. Optionally, release of excess gas is into the body and/or transdermal.

Alternatively or additionally, a release valve 323 (FIG. 1A) is provided to prevent excessive expansion pressure in compartment 310. Optionally, gas is released through valve 323. Optionally, gas is released into the body. Optionally, gas is released through a percutaneous release valve. In an exemplary embodiment of the invention release port 323 is an over pressure relief valve 323. Over pressure condition inside the expander optionally cause release through valve 323 by mechanical means and/or through control implemented via a microprocessor.

Alternatively or additionally, a semi-rigid or rigid backing 301 may be included within, or bonded to, the expandable compartment 310 (see FIGS. 1B and 1C). Backing 301 may, for example, provide an orientation or anchor within the body. Alternatively or additionally, backing 301 may direct expansion of compartment 310 in a desired direction and/or provide a fixed aspect. In an exemplary embodiment of the invention, a breast expansion device 300 includes a semi-rigid siliconized rubber disc 301 that can be deployed between skin and muscle and/or among or between muscle fiber bundles and/or beneath a muscle layer (e.g., pectoral muscles in breast reconstruction). This optionally prevents unwanted pressure on the ribs. Optionally, operative components of the device can be mounted on rigid disc 301 (FIG. 1B).

As depicted in FIGS. 1A-1D gas source 210 and/or valve 100 and/or actuator 200 may optionally be contained within expandable compartment 310. This protects these components and/or gives a natural contour to the body of the subject by concealing their rigid outlines. Alternatively or additionally, this configuration may make the subject less aware of the presence of more rigid components of device 300 by using expandable compartment 310 as a cushion. For example, a subject attempting to grow new skin on their face (e.g., for autologous graft) may be fitted with a device 300 in their right cheek. If source 210 and/or valve 100 and/or actuator 200 were installed adjacent to compartment 310, the subject might feel these components, for example while trying to sleep on the right side. By installing these components inside expandable compartment 310, they are hidden within an inflatable cushion and the subject becomes less aware of their presence. Optionally, inflatable cushion/compartment 310 permits the subject to fall asleep more easily. Similar considerations apply for breast expansion embodiments.

In an exemplary embodiment of the invention, tissue expansion applications which require small expansion volumes, sufficient filling of source 210 may be achieved with a gas that remains in the gas phase in source 210. In an exemplary embodiment of the invention, a face expander 300 employs a small amount of gas. For these types of small expansion applications, gases that are both compressible and biologically safe might be employed. Examples of compressible biologically safe gases include, but are not limited to, oxygen, nitrogen, argon, xenon and neon etc.

The subject in whom the device is implanted may control expansion of the expandable chamber using an external control unit 350 (FIG. 1A). Optionally, the system includes a power source located in the external control unit, which can provide power to the implantable portion. In an exemplary embodiment, the subject presses a button 360 (FIG. 1A) on external control unit 350 to trigger an inflation event (e.g., by issuing an operational command). Optionally, a single activation signal to the actuator opens the valve for a preset amount of time (e.g., 3 seconds), or a preset flow volume through the valve (e.g., 15 ml). In an exemplary embodiment, imposition of a finite limit on the response to the activation signal can serve as a safety feature.

Figure 1D:
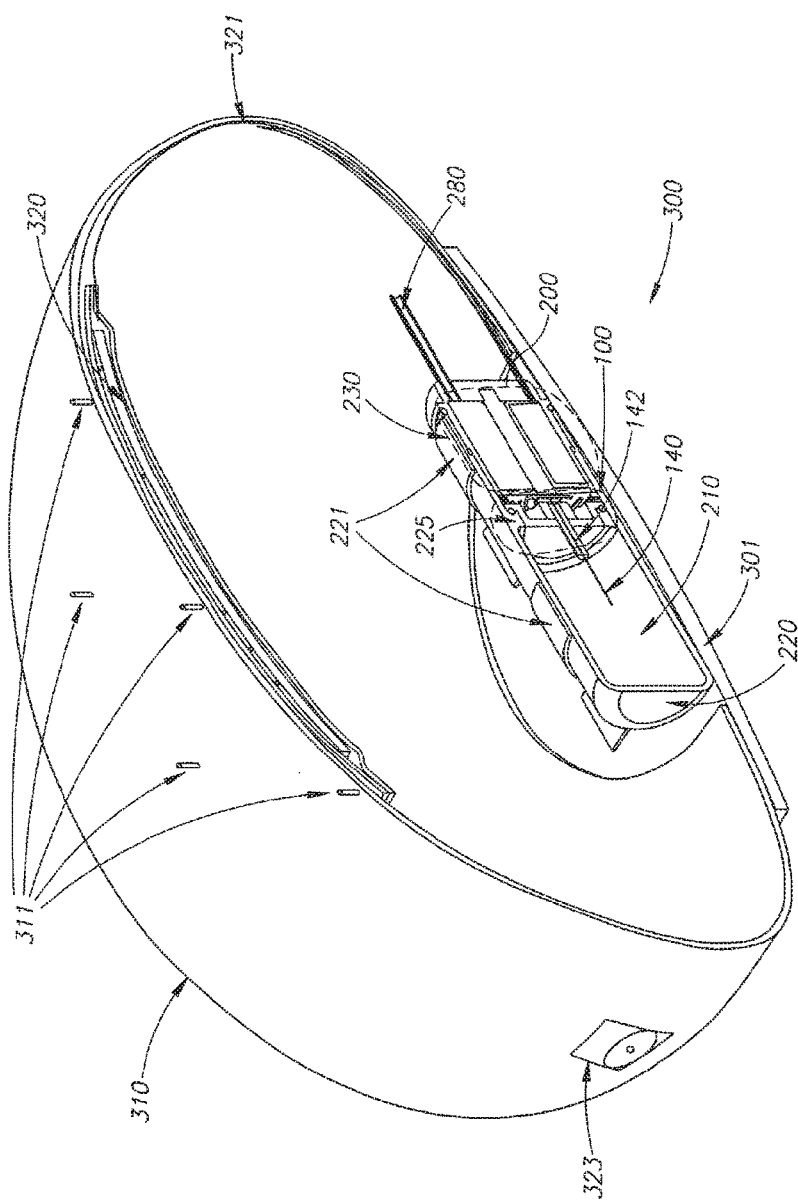
FIG. 1D illustrates a sectional view of an exemplary implantable portion of a tissue expander system.

In an exemplary embodiment, the driver is in communication with a communication component such as an antenna (e.g. an RF coil) 320 mounted on a wall of expandable compartment 310. Optionally, antenna 320 is mounted inside compartment 310 as shown in FIG. 1D. Optionally, this is accomplished by sandwiching between 2 layers of material as pictured. Alternatively or additionally, connection 321 between antenna 320 and actuator 200 follows the contour of compartment 310. Optionally, anchoring studs 311 help insure that antenna 320 remains close to the skin surface and/or in a known location. Optionally, source 210 and/or actuator 200 are anchored to base 301 with retention straps 221, visible in FIG. 1D.

A companion antenna 322 in controller 350 communicates with the antenna in the implantable portion without a physical percutaneous link. These signals may be from the device to the control unit and/or from the control unit to the device. Optionally, the signal includes power and/or data. In order to conserve power and/or to prevent accidental signaling, antennae 320 and 322 may be configured to work only over very short distances (e.g., 5 to 25 mm). Optionally, antennae 320 and 322 are circular and function as coils with near field coupling. In an exemplary embodiment of the invention, the control unit is small and portable and may be operated by either a doctor or by the subject in whom the device is implanted. Alternatively or additionally, antenna 322 may include induction coils which may be used to power operative components of device 300, such as actuator 200. This configuration can be used so external controller 350 provides a safe and reliable means of controlling transfer of gas from the gas source 210 to expandable compartment 310 by separating the power source from actuator 200. This assures that actuator 200 operates only when controller 350 is in close proximity to device 300, thereby preventing accidental inflation of compartment 310 of device 300.

Optionally, it may be desirable for the implantable portion to impart a natural body contour, for example in breast reconstruction. The expandable chamber may be formed from a deformable inelastic material which is pre-molded to a desired shape. This may be accomplished, for example, by welding or vacuum molding two sheets of material together. Alternatively or additionally, pleats or folds may be used to impart a desired shape. Desired shapes optionally include partial spheres (e.g., hemisphere), offset partial sphere or breast (tear) shaped.

In an exemplary embodiment of the invention, a studded surface is employed for anchoring so that protruding studs penetrate the overlying pectoralis muscle in order to prevent movement of the device with respect to the muscle. Optionally, studs are installed on an anterior surface. Optionally, 1-500, optionally, 2-350, optionally 3 to 75, optionally 4 to 50, optionally 5 to 25, optionally 6-10 studs of 2-3 mm in height are sufficient for anchoring. In an exemplary embodiment of the invention, the small number of studs provides a desired degree of anchoring but does not contribute to difficulty in removing the device. Optionally, the studs are resorbable. In an exemplary embodiment of the invention, once a capsule has formed to stabilize the position of the device, the studs are resorbed.

FIGS. 2-6 illustrate exemplary additional embodiments of tissue expander systems and methods of use, additional details of which are described in U.S. Pub. No. 2011/0152913, published Jun. 23, 2011.

Figure 2:
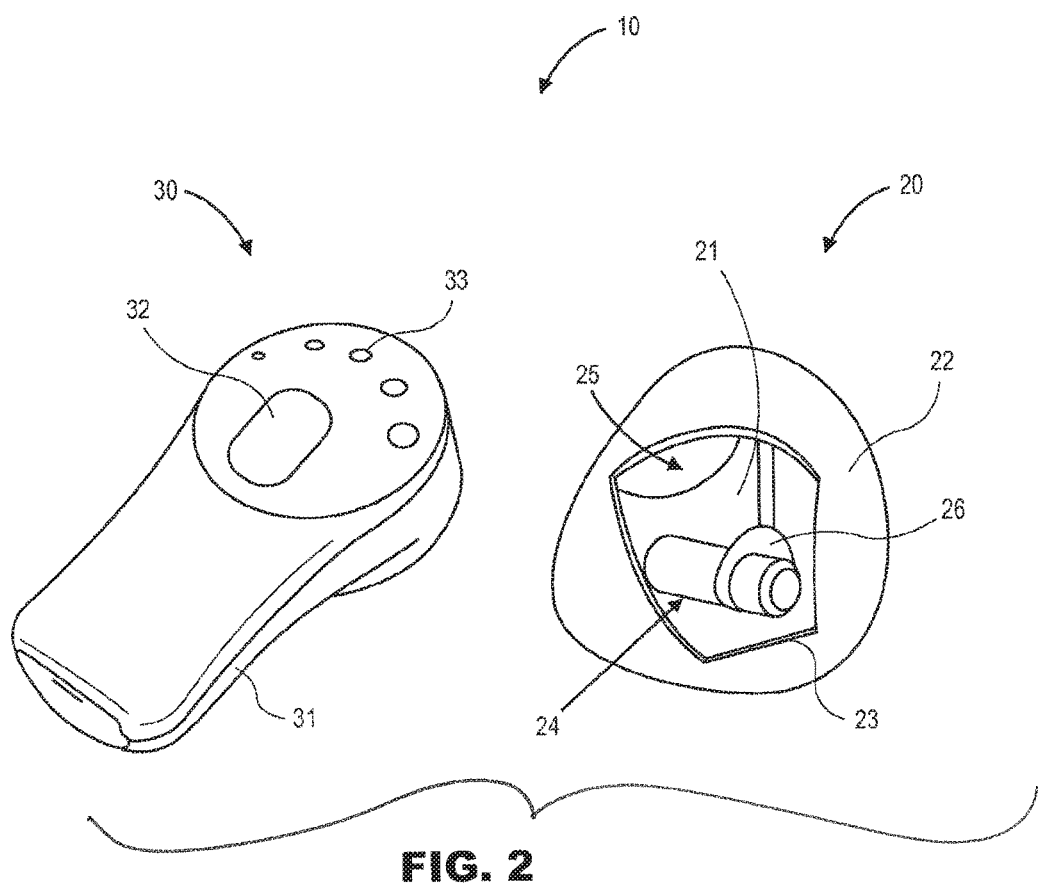
FIG. 2 illustrates an exemplary tissue expander system including a remote controller and an implantable portion.

FIG. 2 illustrates an exemplary embodiment of a tissue expansion system. Tissue expansion system 10 includes implantable portion 20 (also referred to herein as "implant") and remote controller 30. In this embodiment the implantable portion has a general breast shape or configuration and is adapted for breast reconstruction following, for example, mastectomy. Implantable portion 20 includes outer shell 22 and an inner portion (also referred to herein as an "inner bag"), which comprises anterior portion 23 and posterior portion 21. A portion of the outer shell and the anterior portion of the inner bag are shown removed to illustrate additional components of the implant. The inner bag defines an expandable chamber, or compartment. Implant 20 also includes fluid reservoir and valve 24 (when combined are commonly referred to herein as a "driver"), as well as communication component 25. The driver and the communication component are positioned completely within the inner bag and secured thereto, either directly or indirectly. In FIG. 2 driver 24 is secured to cradle 26, which is secured to posterior portion 21 of the inner bag.

Tissue expansion system 10 also includes remote controller 30, which is generally adapted to wirelessly communicate with and provide power to the implantable portion via communication device 25 to control the release of fluid from the fluid reservoir into the expandable inner chamber. Remote controller includes housing 31, actuator 32, and output 33. Actuator 32 is shown as an actuatable button, while output 33 is shown as a plurality of visual indicators (e.g., LEDs). The actuator in the remote controller can be any other suitable actuator (e.g., a knob, a microphone adapted to receive a user's voice as input, etc.). The output can provide any number of different types of output to communicate information, such as, for example, visual, audio, tactile, etc.

Figure 3:
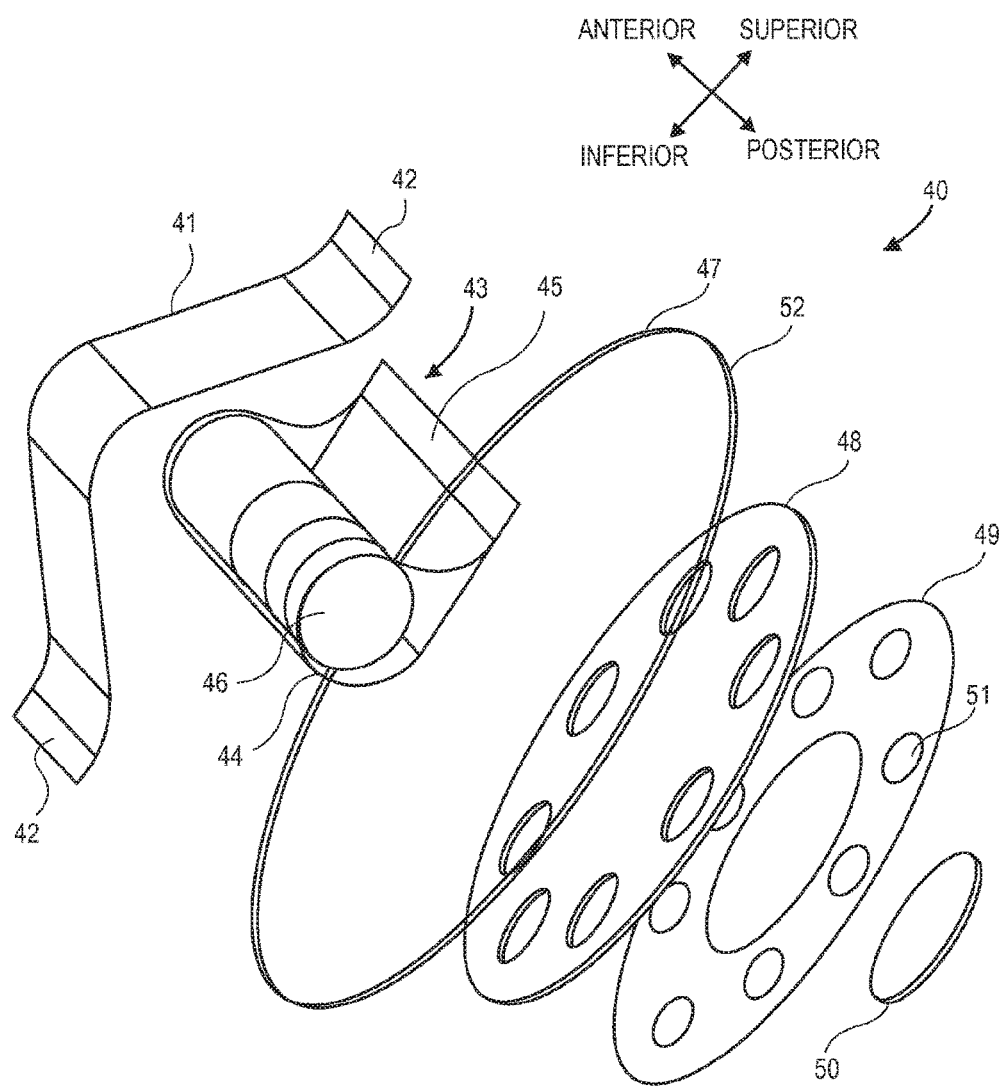
FIGS. 3 and 4 illustrate an exemplary exploded view of a backing and driver of an exemplary implantable portion of a tissue expander system.
Figure 4:
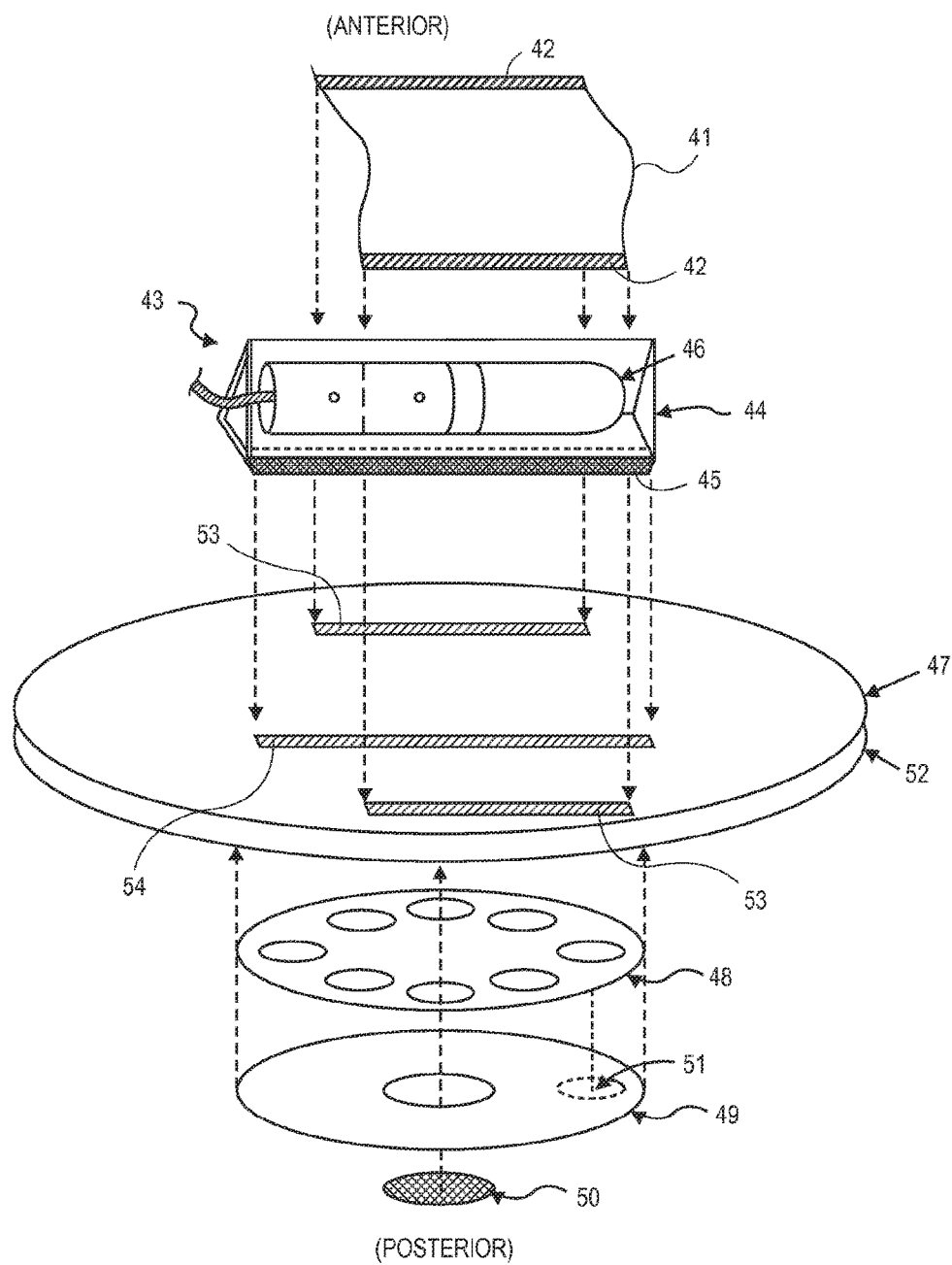

FIGS. 3 and 4 illustrate exploded views of a portion of an alternative embodiment of an implantable portion. FIG. 4 illustrates in greater detail the alignment of the components of the assembly. FIG. 3 illustrates generally the posterior portion of the inner bag and the manner in which the driver is secured thereto. The portion of implant 40 illustrates a general "hammock" design which allows the driver to be secured to the implant but where it is not rigidly fixed to the expandable chamber. This design provides for a greater degree of movement between the driver and the inner bag. The embodiment in FIG. 3 also reduces the "height," or projection of the driver in the anterior direction. The portion of the implant shown includes film band 41, hammock 43, driver 46, posterior panel barrier film 47, posterior panel 52, sheeting material 48, barrier ring 49, and outer patch 50. In a merely exemplary embodiment, the components are made of the following materials: film band 41 is a polyethylene film; hammock 43, which includes film 44, is a polyethylene film, posterior panel barrier film 47 is a polyethylene/polyvinylidene chloride ("PVDC") film; sheeting material 48 is a textured silicone material; barrier ring 49 is a polyethylene/PVDC film; and outer patch 50 is a silicone material.

In an exemplary assembly of the implant shown, ends 42 of film band 41 are heat-staked to posterior panel barrier film 47 at seal areas 53 (shown in FIG. 4). Seal area 45 of film 44 is heat-staked to posterior panel barrier film 47 at seal area 54. The heat-staking secures hammock 43 to posterior panel barrier film 47. End 45 of hammock 43 is superiorly positioned to allow driver 46 to "hang" within hammock 43. Barrier ring 49 is heat-staked to posterior panel 52 at the eight (8) seal areas 51 (only one is shown in FIG. 4), which secures silicon sheeting material 48 between barrier ring 49 and posterior panel 52. Outer patch 50 is secured to sheeting material 48 using silicone adhesive. Once assembled the portion of the implant 40 can then be secured to the rest of the implant (e.g., the anterior portion of the inner bag and the outer shell).

In the embodiment shown in FIGS. 3 and 4, the height, or projection, of the driver is reduced. Because the driver is not rigidly fixed to the inner expandable compartment, it has more flexibility within the implant. The position of the driver can be slightly adjusted relative to parts of the anatomy to relieve discomfort caused by the driver. For example, the driver can pivot, or rock, if it is located on top of a bony rib, thereby reducing discomfort to the patient. This arrangement allows the driver to be secured to the expandable chamber without being rigidly fixed thereto. While this design does provide for movement of the driver within the implant, film band 41 acts to prevent the driver from moving around too much due to patient movement (e.g., jumping, driving over bumpy terrain, etc.).

Figure 5:
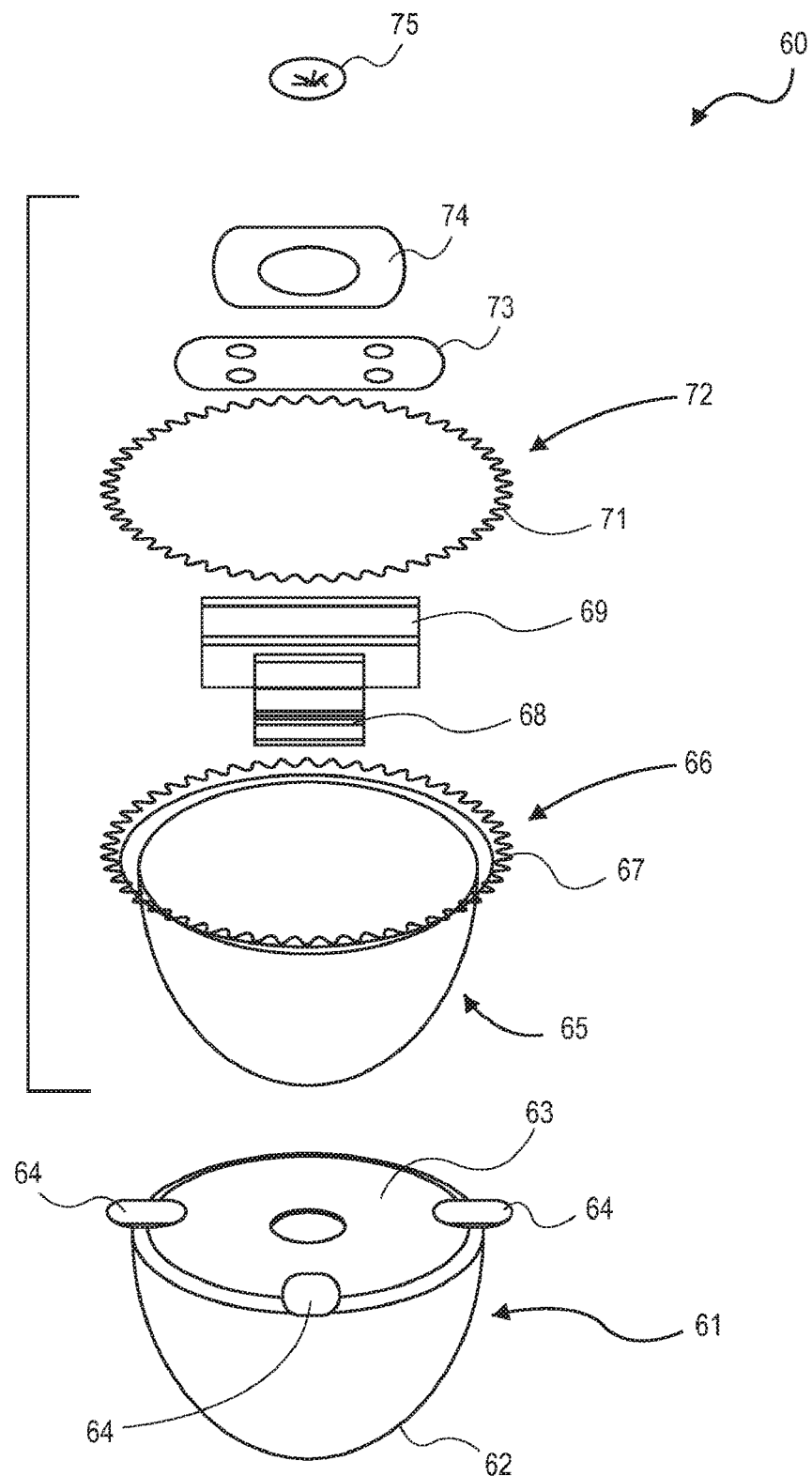
FIG. 5 is an exploded view of an exemplary implantable portion including an outer shell disposed around an inner bag, or inner portion.

FIG. 5 illustrates an alternative embodiment of an implantable portion (driver and implant antenna not shown). The inner bag includes generally breast-shaped anterior portion 65, which has a perimeter seal 66 with a serpentine cut that creates a plurality of fingers 67. The inner bag also includes posterior portion 72, which also has a serpentine cut around a perimeter seal to create a plurality of fingers 71. In an exemplary method of manufacturing, phone dial film 74 is heat staked to posterior portion 72 through phone dial 73. Hammock 69 and band 68 are heat staked to the inner surface of posterior portion 72 as in the embodiment in FIGS. 3 and 4. The perimeter of anterior portion 65 is heat staked to the perimeter of posterior portion 72, forming the inner expandable chamber. The inner portion, once assembled, is then placed within outer shell 61, which comprises anterior portion 62 and posterior portion 63. Anterior portion 62 and posterior portion 63 can be integral, or they can be separate components secured together. Identifier 75, which can include information identifying the implant, is secured to phone dial 73 after the inner bag is placed within shell 61. The implant also optionally includes at least one suture tab 64, which can be used to help secure the implant to tissue within the subject. Sutures can be used to secure the suture tabs to tissue within the patient, thereby securing the implant within the patient. The suture tabs 64 can be secured to the implant after assembly with adhesive, such as silicon adhesive.

In some embodiments the perimeter formed when the perimeters of anterior portion 65 and posterior portion 72 are heat staked together can become rigid and may cause discomfort when implanted. The embodiment in FIG. 5 includes serpentine cuts in the perimeters of both anterior portion 65 and posterior portion 72, which create the fingers described above, to reduce the amount of rigidity in this region. In some embodiments all of the fingers are heat staked together, while in some embodiments less than all of the fingers are heat staked. In some embodiments at least one of the fingers is cut off or trimmed to reduce the stiffness of the finger region.

In one or more exemplary embodiments, the components of the implantable portion can be made from the following materials: the outer shell comprises silicone rubber; the suture tabs comprise silicone rubber with polyester (Dacron) reinforcement; the inner bag is a barrier film; the hammock and the band are either polyethylene or barrier film; and the phone dial and the phone dial film are silicone rubber.

In the embodiments in which the fluid is $CO_2$, the inner bag provides a barrier to $CO_2$ after it has been released from the gas reservoir.

In some embodiments the inner bag or chamber is at least partially made from a non-elastic material and is pre-formed, such as, for example without limitation, a breast shape with a lower pole extension. The inner chamber will expand towards the anatomical shape (not necessary reaching the exact preformed configuration) when the fluid is released from the reservoir into the internal chamber. This responds unlike a liquid-filled elastomeric balloon, which does not have a preformed shape to which the balloon expands when filled with a liquid. When the inner bag has a preformed shape of a breast, the expanded shape emphasizes lower pole expansion where tissue generation is particularly desired during breast reconstruction so that the skin assumes the shape of a breast. FIGS. 2 and 5 are exemplary embodiments in which a substantially inelastic portion of the implant has a breast configuration or shape. In particular, in these embodiments the inner chamber comprises the inelastic component that has the general breast shape.

In some embodiments the inner bag comprises multiple layers of material that are sandwiched together to form the inner bag. Exemplary materials which may be utilized in the inner bag can be found in U.S. Pat. App. Pub. 2006/0069403, filed Sep. 21, 2005, which is incorporated herein by reference. In some embodiments the inner bag roughly has the thickness of a piece of paper, and while it has the ability to stretch a relatively small amount, it does not have properties like an elastic film. To form the inner bag in a desired anatomical shape, any layers which make up the inner bag are positioned adjacent one another with the desired layering, heated, applied to a mold which has the desired shape, and then allowed to cool on the mold. The mold is then removed. In the embodiment in FIG. 5, for example, any layers that make up anterior portion 65 can be formed on a mold as described above.

A pre-formed configuration also prevents the expandable chamber from expanding into undesirable shapes since the inner bag will tend to expand into its pre-formed shape. This is unlike, for example, a hot-dog shaped elastomeric balloon, which, if squeezed in the middle, will become a dog-bone shaped balloon. Forming the inner bag in the shape of a breast, for example, prevents the implant from expanding laterally (under an arm) or superiorly (toward the clavicle). The shape of the tissue to be expanded can therefore be controlled by forming the inner bag into a particular shape.

In some embodiments the fluid source is a gas source, and in some embodiments the gas is, for example without limitation, $CO_2$. In some embodiments the gas reservoir has an internal volume of about 1 cc to about 50 cc, and in some embodiments is about 2 cc to about 10 cc. In an exemplary embodiment, a compressed gas source has a total internal volume of about 5 ml. Optionally a large tissue expansion may be achieved by providing about 2.5 grams of $CO_2$ in a 5 ml internal-volume container. This provides about 1200 ml of $CO_2$ at 15.5 PSI (0.8 PSI above atmosphere at sea level). The exact amounts may vary, but in some embodiments a constant ratio can be used. For example, for every 1 mL of internal volume container filled with 0.5 grams of $CO_2$ gas, there is about 240 mL final volume (at 0.8 PSI). The reservoir can be encased in a leak-free canister.

The outer shell generally provides a tissue interface for the implantable device. In some embodiments the outer shell is comprised of silicone, but can be made of any other suitable material. It can be smooth, but in some embodiments the outer shell is textured to help stabilize the implant within the patient. When the outer shell is a silicone outer shell, the silicone outer shell provides little resistance to the permeation of $CO_2$.

The implantable portion of the tissue expansion system includes a communication component, which can include an antenna, to facilitate communication with the remote controller. In some embodiments the communications component is secured to an anterior portion of the inner bag to provide for the easiest coupling between the remote controller and the antenna when the remote controller is held close to the patient's body in the region in which the implant is positioned. For example, in the embodiment in FIG. 2, communications component 25 is secured to the anterior portion of the inner bag. Communications component 25 is also secured to a superior portion of the inner bag, which can make it easier for the remote controller to communicate with the communications portion of the implant.

Figure 6:
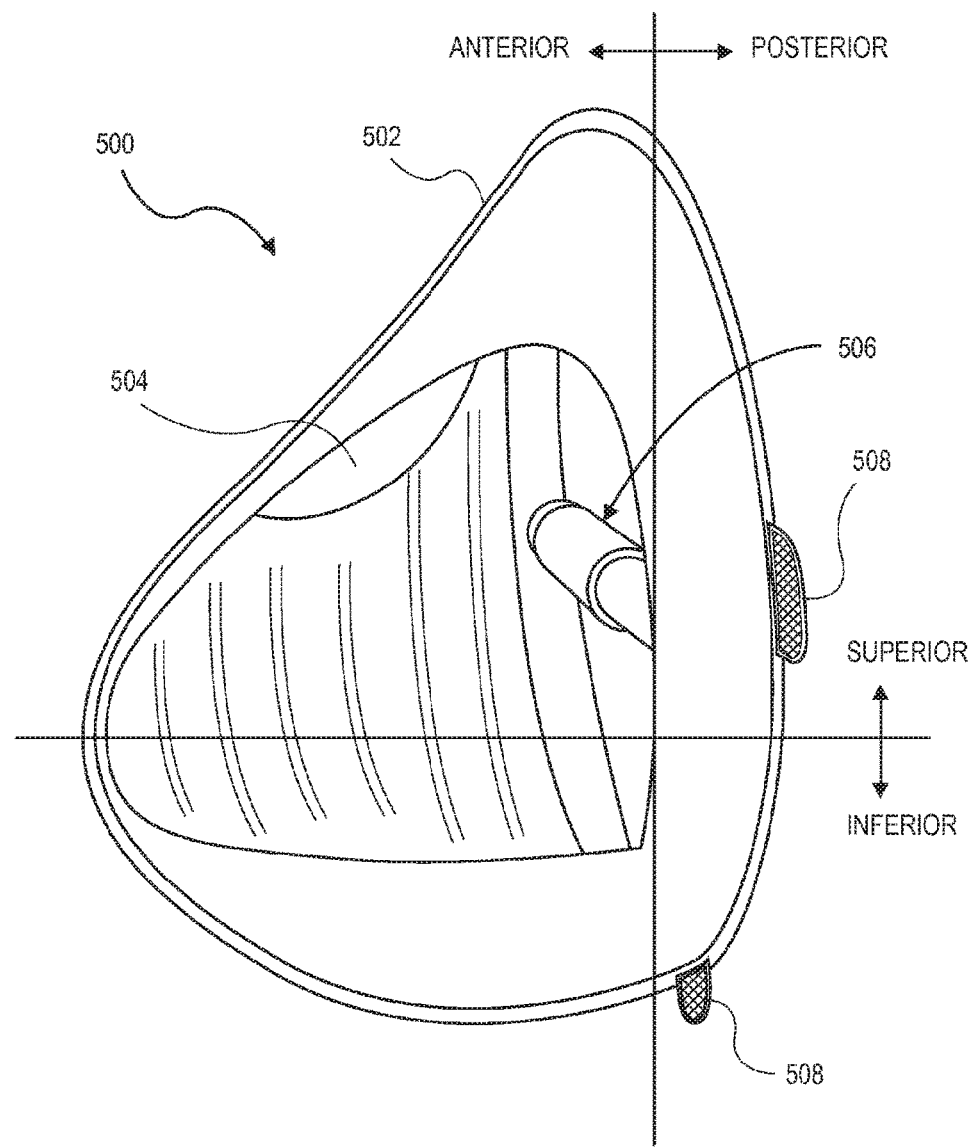
FIG. 6 illustrates an exemplary implantable portion, with a section removed to visualize a portion of the expandable chamber.

FIG. 6 illustrates an exemplary implant 500, which includes inner bag 502 (outer shell not shown) with a section removed to reveal communications component 504 and driver 506, both of which are secured to inner bag 502. Implant 500 also includes suture tabs 508 (a third tab is not shown). In general, the inner bag has anterior and posterior portions as indicated. In this embodiment, the posterior portion generally refers only to the backing, or the generally flat portion, of the inner bag. The curved portions of the inner bag are generally considered the anterior portion. Additionally, the inner bag has an inferior portion and a superior portion as shown. The implant can be considered to be divided into 4 quadrants, based on the planes separating the anterior/posterior portions and the superior/inferior portions. As shown, the antenna is secured to the anterior portion and the superior portion of the inner bag to make the coupling between the remote controller (not shown) and communication component 504 as efficient as possible.

In embodiments in which the inner bag has a pre-formed expanded configuration, the communication component is attached to a complex 3-dimensional shape in which the inner bag is formed. The communication component, however, has the ability to deform the shape of the inner bag when secured thereto due to the weight and stiffness of the communication component. In some embodiments, in order to secure the communication component to the inner bag without altering the shape of the inner bag, the communication component is first encapsulated in a film layer, which is then secured to the inner bag. During attachment of the encapsulated communication component, the formed membrane has the ability to provide an approximately uniform amount of pressure over the communication component while it is attached to the inner bag. A material such as an ESCAL™ bag can be used as the membrane to provide the necessary amount of pressure to the encapsulated communication component while being laminated to the inner bag. This will prevent the inner bag from losing its preformed shape. Additionally, the communication component is positioned on the anterior portion of the inner bag to maintain its position as close as possible to the surface of the patient. This improves the communication component's electromagnetic coupling with the remote controller.

The implant also includes a driver, which comprises a fluid reservoir and a valve, which controls the flow of fluid from the reservoir. In some embodiments the fluid reservoir is a compressed gas source. Actuation of the remote controller can open the valve to controllably releases gas from the reservoir into the inner chamber.

After the implantable portion is positioned within the patient, the remote controller is actuated to release the fluid from the fluid reservoir, through the valve, and into the inner chamber. A "burp" is referred to herein as the event in which fluid is released from the reservoir. The periodic or continuous release of the fluid into the expandable inner chamber causes the inner chamber to expand over time, which causes the expansion of tissue proximate the implant. Once the tissue has been expanded to the desired degree of expansion, the implant can be removed from the patient and a permanent implant can replace the temporary implant.

The remote controller is adapted to control the amount of fluid that is released from the fluid reservoir over time. When the user actuates the actuator on the remote controller, the valve within the driver opens and releases the fluid, such as $CO_2$, from the reservoir into the expandable inner chamber.

The tissue expansion system comprises various electronic components to perform the functions described herein. The electronic components can be disposed in the remote controller, the implant, or some of the electronics can be disposed in the controller while some are disposed in the implant. In general, the tissue expansion system includes electronic components that allow the remote controller to wirelessly communicate with the implant and provide power thereto to control the release of fluid from the fluid reservoir. In some embodiments, such as those described above, the implant includes an antenna adapted to communicate with the driver. The antenna is adapted to be electromagnetically coupled with an antenna in the remote controller upon actuation of the remote controller such that actuation of the remote controller induces current to flow through the solenoid coil to open the valve, thereby releasing the fluid from the reservoir. In this manner the remote controller is adapted to provide power to the implantable implant via inductive coupling. In order to facilitate the transmission of temporary power to the driver, the antenna of the external device and the implantable devices must be in within a certain range of each other. Transmission of power between the remote controller and the implant can alternatively be carried out through a radiofrequency link or other types of wireless links.

In some embodiments the remote controller includes a power source, such as a rechargeable battery, to provide power to some or all of the system's electronic components. The implantable portion may also comprise a power source to provide power to electronic components within the implantable portion.

In some embodiments the implantable fluid is $CO_2$, and the $CO_2$ will leak out of the inner bag/outer shell assembly over time. While the inner bag can be adapted to provide for a $CO_2$ barrier, some $CO_2$ will diffuse through the layers of the inner bag over time. $CO_2$ can diffuse through the molecular structure of polymers, and is essentially impossible to completely contain within polymeric material. To determine the level of $CO_2$ permeability through an inner compartment, a known amount of $CO_2$ is released into an inner compartment, and the inner compartment is submersed in saline. $CO_2$ will diffuse through the inner compartment over time and into the saline. Periodic measurements of the volume of the inner compartment are made over time, which provides for an estimate of the rate of $CO_2$ permeation. In some embodiments the inner compartment is permeable between about 0 and 3 mL/day.

Figure 7:
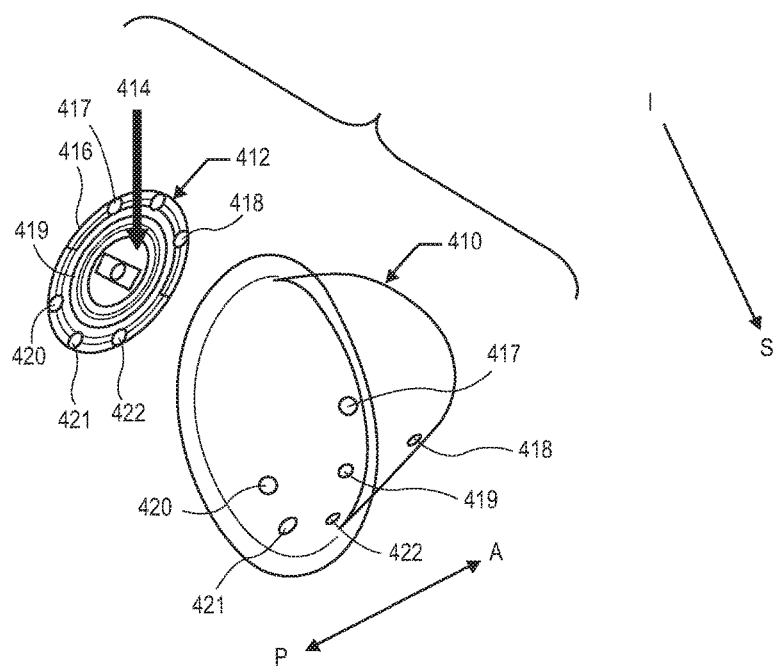
FIG. 7 is an exploded view of a communication component and an anterior layer of an exemplary implantable portion.
Figures 8A, 8B:
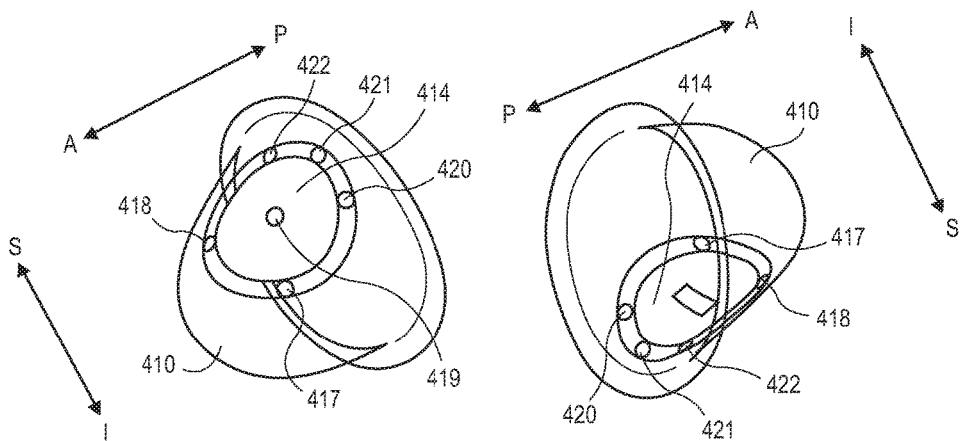
FIGS. 8A and 8B illustrate the assembled communication component and anterior layer from FIG. 7.

FIGS. 7, 8A and 8B illustrate an exemplary embodiment of a portion of an implantable portion of a tissue expander system. The implantable portion includes an antenna 414 that is movably secured to anterior panel 410 of an expandable chamber. Anterior panel 410 generally defines at least a portion of the expandable chamber, and in this embodiment defines an anterior portion of the expandable chamber. Although not shown, anterior panel 410 is secured to a posterior panel, or backing, of the expandable chamber, as described herein. In this embodiment the antenna is adapted to receive and/or send wireless signals with an external remote controller as described herein. The remote controller is actuated to communicate with the antenna, which activates the release of gas from the compressed gas reservoir, examples of which are described in more detail herein. The antenna is secured to the anterior portion of the implant to allow for easier communication with a remote controller due to the shorter distance, but the antenna could also be secured to the posterior backing of the implantable portion as well.

In general, the expandable chamber of the implantable portion includes a relatively thin-walled portion, and an antenna secured to the thin-walled portion will generally be stiffer than the wall. When the implant is manipulated by a physician during insertion, the physician inherently manipulates and distorts the anterior panel to some degree. This creates loads on the antenna. Additionally, after implantation, the antenna undergoes loads as the inflatable chamber is inflated with gas from the compressed gas reservoir. There is thus a risk that the stiffer antenna will damage the wall of the expandable chamber.

An implant that is configured to allow for some movement between the antenna and the expandable chamber to which it is secured will beneficially reduce or eliminate damage to the wall. In the embodiment in FIGS. 7, 8A, and 8B, the antenna is movably secured to a communication member 412, which in this embodiment has a general pocket configuration that includes two sides or portions in between which the antenna is movably disposed. The communication member similarly is secured to the anterior panel 410 of the expandable chamber in such a way that there is some movement that can occur between the communication member and the expandable chamber. In this embodiment there are thus two ways in which relative movement between components creates a reduced risk of damage to the expandable chamber to which the antenna is secured.

The following provides an exemplary method of assembling the anterior panel and communication component subassembly shown in FIGS. 7, 8A, and 8B. The steps need not be carried out in the specific order, and some steps may be left out of the method if the method is modified such that the steps are optional. An antenna pocket is first created by bonding a film ring between two film discs. In FIG. 7 the bonds are indicated by the darkened region 416. A portion of the antenna pocket is then bonded to anterior panel 410 at bond locations 417, 418, and 419. Antenna 414 is then inserted into the antenna pocket and bonds are formed between the two sides at discrete locations 420-422. Bonding of the pocket is then completed by bonding the antenna pocket (with antenna therein) to anterior panel 410, this time at locations 420, 421, and 422. More or fewer bonding locations can be used. The antenna is disposed within the pocket and is able to float within the antenna pocket. Additionally, the pocket is attached directly to the inside of the expandable chamber at a plurality of discrete locations rather than all the way around the periphery of the pocket. The areas where the pocket is not directly secured to the expandable chamber allow for some movement between the antenna pocket and the expandable chamber wall, allowing for less stress in the expandable chamber, and reducing the likelihood of damage to the expandable chamber wall. In this embodiment the antenna is movably secured to both the communication component 412 and the wall of the expandable chamber 410.

As set forth above, anterior panel 410 and communication component 412 are components of an implantable portion of a tissue expansion system, and can be incorporated into any of the tissue expander systems described herein.

FIG. 7 is an exploded view showing communication component 412 and anterior panel 410 before they are coupled together. The anterior "A" and posterior "P" directions are indicated, and reflect the relative positioning of the device as would be positioned within a patient's breast. Inferior "I" and superior "S" directions are also indicated. FIGS. 8A and 8B are assembly views, with FIG. 8B being from the same perspective as FIG. 7. FIG. 8A is from a generally superior and anterior view.

In some embodiments the fluid that is used to expand the expandable chamber is a gas, such as from a compressed gas source. A gas source can be external to the patient, positioned within the patient and outside the expandable chamber, inside the expandable chamber, or partially inside and partially outside the expandable chamber. It may be beneficial to have, in addition to the expandable chamber layer (which may be referred to herein as a wall or surface), a second wall (or layer) disposed outside of the expandable chamber layer and adjacent to the expandable chamber wall that helps act as a gas barrier layer to reduce the gas permeation rate out of the expandable chamber. Reducing the permeation, if desired, can be a significant advantage in that inflation of the inflatable chamber is much more controlled and reliable. Gas permeation out of the chamber can, without a corresponding amount of new gas being released into the inflatable chamber, reduce the overall inflation of the inflatable chamber and can thus slow or prevent the desired tissue expansion. By reducing permeation the inflation and thus tissue expansion (e.g., pocket creation) can be controlled in a much more reliable manner. An added layer or wall outside of the expandable chamber wall can provide that significant advantage. Additional considerations for gas permeability and material selection can be found herein.

Figure 9:
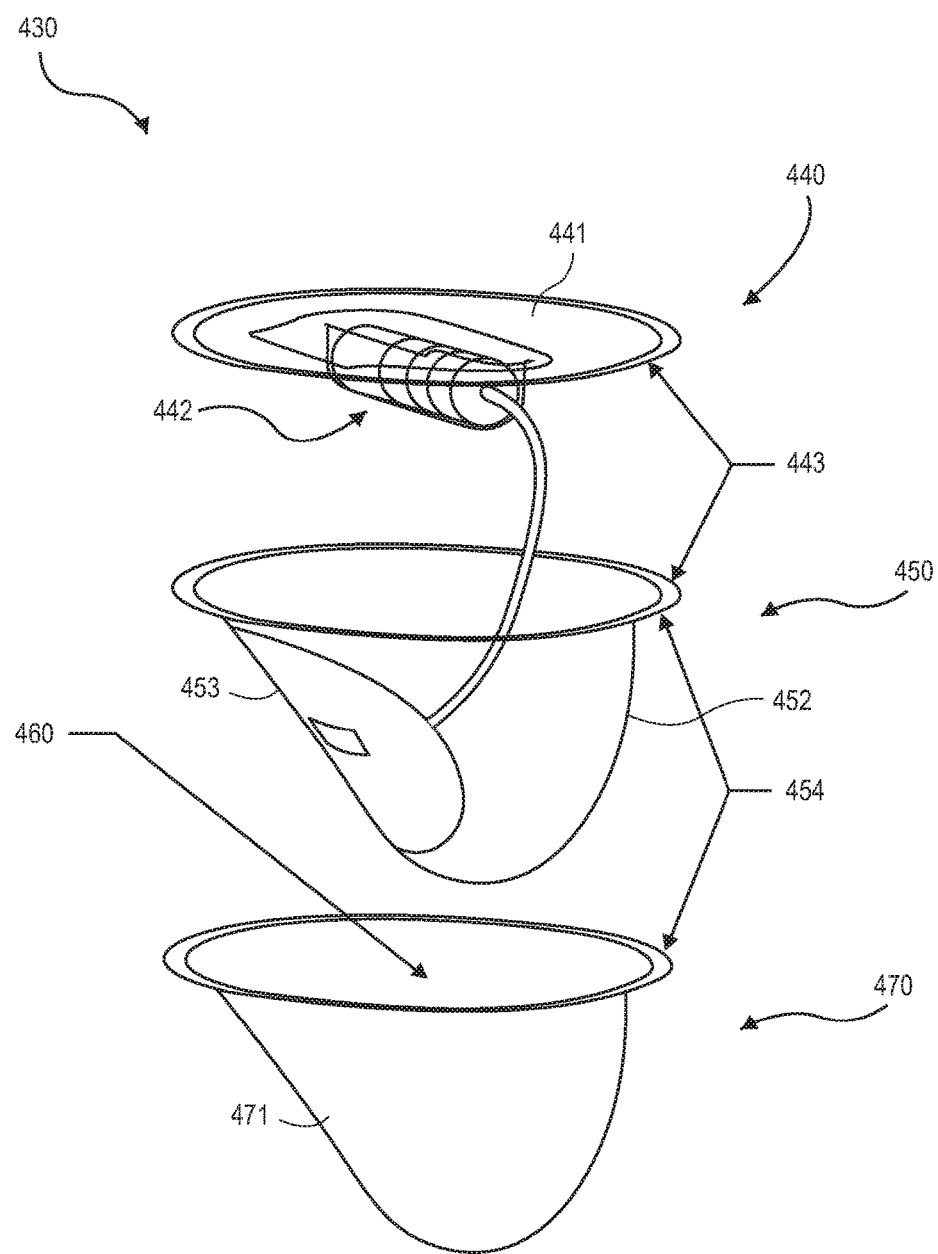
FIG. 9 is an exploded view of an inner portion of an exemplary implantable portion. The inner portion includes an inner member and an outer member.

FIG. 9 is an exploded view of an exemplary inner portion, or inner bag, 430 of an implantable portion of an exemplary tissue expander system. Inner portion 430 can be used with any of the tissue expanders systems described herein. In some embodiments inner portion 430 is positioned inside an outer shell, such as an elastic outer shell, examples of which are described herein. Inner portion 430 includes a posterior portion 440 and an anterior portion that includes anterior inner layer 450 and anterior outer layer 470. "Inner layer" 450 and "outer layer" 470 may be referred herein as an "inner member" and an "outer member." Both the inner member 450 and the outer member 470 are deformable. Posterior portion 440 includes backing 441 secured to driver assembly 442, examples of which are described herein. In some embodiments anterior inner layer 450 includes anterior panel 410 and communication component 412 shown in FIGS. 7, 8A, and 8B. In this embodiment inner layer 450 is a deformable member comprising an inelastic material 452 that is molded to have a pre-formed configuration (e.g., a breast configuration with a lower pole extension) and is adapted to be reconfigured towards the pre-formed configuration when the inflatable chamber is inflated with gas from the compressed gas reservoir. Exemplary methods of forming the inelastic material into a desired pre-formed configuration such as the configuration with the lower pole extension are described herein. Inelastic member 452 can in some embodiments be comprised of multiple plies of a multi-layer barrier film with the outer layers being polyethylene, which enables heat sealing/staking with other polyethylene components, and the barrier material can be PVDC (polyvinylidene chloride). Anterior outer layer 470 includes inelastic member 471 which is in some embodiments a single ply of a multi-layer barrier film with the outer layers being polyethylene, which enables heat sealing/staking with other polyethylene components. Inelastic element 471 is in this embodiment also pre-formed with a, for example without limitation, general breast configuration with a lower pole extension in the same manner as is inelastic element 452. In some embodiments inelastic element 471 includes PVDC, and thus can include the same material as in inelastic element 452. The two inelastic elements need not be the same material, however, nor do they need to have the same general pre-formed configuration if they both do have pre-formed configurations. Anterior outer layer 470 is secured to anterior inner layer 450 by heat staking at the outer perimeter 454. Anterior inner layer 450 is secured to posterior portion 440 by heat staking at the outer perimeter 443. In this embodiment both the inner and outer members comprise inelastic materials with pre-formed configurations that are generally the same, as can be seen from FIG. 9. By having two (or more) layers in the inner portion as shown by the two members 450 and 470 in FIG. 9, permeation of the gas out of the inner portion is significantly reduced.

Outer member 470 can also provide additional benefits. In some uses, tissue that is adjacent the implant, can, without an outer member, cause the inner member to fold in certain places. For example, if the implant is placed sub-muscular, the muscle moving over the implant can cause rolling folds in the inner member. Erosion or damage of the material can occur over time at the location of the folds, possibly causing the inner member to rupture or exhibit increased permeation in the case of a gas filled implant. An outer member, such as outer member 470, can thus act as a relatively lower friction interface so that as tissue adjacent the implant moves the outer member can move relative the inner member, reducing the amount of moving that occurs in the inner member. Damaging folding and/or erosion in the inner member are thereby reduced. Reducing the movement and folding that occurs in the inner layer by incorporating an outer layer can thus protect the inner layer's integrity and reduce the likelihood of damage and rupture.

Having an outer member or layer disposed outside of a chamber can also be beneficial even if the fluid inside the chamber is not a gas, and even if the chamber is not filled with fluid from a fluid source. For example, an outer layer added to a silicone filled breast implant could provide advantages over a single filled chamber. As described herein, erosion or damage of the material can occur over time at the location of the folds in the inner member, possibly causing the inner member to rupture. This outer member can act as a relatively lower friction interface so that as tissue adjacent the implant moves the outer member can move relative the inner member, reducing the amount of moving that occurs in the inner member reducing the damaging effect of folds. In some embodiments the outer layer, such as outer layer 471, has a thickness that is less than a thickness of inner layer, such as inner layer 452. By having a thickness in the outer layer that is less than a thickness of the inner layer, the outer layer can be folded with less damage to the outer layer. It also moves more easily in response to adjacent tissue (e.g., muscle) movement, and the tissue movement is less likely to drag a section of folded inner member with it. The outer member is thus both less likely to be damaged when folded and to damage the inner member in response to tissue movement.

In some of the embodiments herein the inner layer is between about 75 microns and about 150 microns thick, and the outer layer is between about 25 microns and about 75 microns thick. In some embodiments the inner layer is between about 75 microns and 100 microns thick. In some embodiments the thickness of the inner layer is greater than the thickness of the outer layer. In some embodiments the thickness of the inner layer is at least 1.5 times the thickness of the outer layer (e.g., 50 microns thickness outer and 75 microns thickness inner). In some embodiments the thickness of the inner layer is at least 1.75 times the thickness of the outer layer. In some embodiments the thickness of the inner layer is at least 2 times the thickness of the outer layer (e.g., 50 microns thickness outer and 100 microns thickness inner). In some embodiments the inner layer is no more than 8 times the thickness of the outer layer (e.g., 25 microns thickness outer and 200 microns thickness inner). In some embodiments the inner layer is no more than 6 times the thickness of the outer layer.

In some embodiments the outer layer can be an elastic component and still provide the benefits described above about reducing erosion to the inner layer. Thus in some embodiments the inner layer can include an inelastic material with a pre-formed configuration and the outer layer can be an elastic material.

In some embodiments a standard known gel-filled breast implant with an elastic material that defines the chamber in which the gel is disposed can be modified to include an outer layer around at least a portion of the implant. For example, the outer layer could extend around the entire implant or could extend around only an anterior portion.

In embodiments that include an outer layer or outer member (e.g., outer member 470) outside the inner member (e.g., inner member 450) a lubricious material can be added between the two members to reduce friction between the two members and thus reduce the likelihood of damage to the inner and outer members. As stated above, the inner and outer members can move relative one other when adjacent tissue moves, which advantageously protects the inner member. A lubricious material between the two members, however, reduces undesired rubbing between the two members, which can also lead to erosion and possibly rupture.

In an exemplary method of manufacturing, prior to bonding anterior outer layer 470 to anterior inner layer 450, a lubricious material 460 is placed or positioned between anterior outer layer 470 and anterior inner layer 450 resulting in increased wear resistance for friction and rubbing on the implant. The lubricious material is generally a biocompatible lubricant, for example without limitation, a silicone based lubricant or other biocompatible lubricant (e.g., NUSIL MED-420, 100 cP viscosity). Other lubricants (biocompatible) and viscosities may be used. Another example of a lubricious material that can be used is soybean oil. Additionally, the lubrication could be provided by a coating on one or both of the inner and outer members. The lubricious substance advantageously reduces shear between the anterior inner member 450 and anterior outer member 470. Alternatively, a material that may not be typically considered lubricious could also reduce the friction between the inner and outer members, such as sterilized saline or water. In the embodiment in FIG. 9, the lubricious material is contained in a chamber, at least part of which is disposed directly between the inner and outer members.

The volume of lubricant can depend on the size of the tissue expander and its intended use, but exemplary volumes that can be placed between layers (or members) of exemplary breast tissue expanders can be from about 0.2 mL to about 2 mL, or between about 0.5 mL to about 1.5 mL. For example, in some specific embodiments the volume is about 0.8 mL±0.2, 1.0 mL±0.2, or about 1.2 mL±0.2. In general, the volume of lubricant is not intended to add thickness to the inner portion of the tissue expander (the thickness being measured between the inner surface of the expandable chamber and the outer surface of the outer member) but instead is used to provide a thin lubricating film. While there will be some marginal thickness added, the addition of lubricant is intended herein to substantially not change the thickness at all.

A traditional breast implant could be enhanced with a lubricous material as well. For example, in some embodiments a breast implant has an elastic material that defines a chamber in which a gel is disposed. The breast implant can also include an outer member that can be an elastic layer, and a lubricous material can be positioned between the inner and outer layers to reduce friction between the inner and outer members.

In some situations gas that has been released into the inflatable chamber will, over time, permeate out of the inflatable chamber. This can prevent the inflatable chamber from maintaining a desired expansion pressure on tissue adjacent the implant. In some embodiments the gas reservoir, which can be a $CO_2$ reservoir, is adapted such that it initially contains more compressed gas than the inflatable chamber is adapted to maintain. If an amount of gas above a certain threshold permeates out of the chamber, or if the internal chamber pressure drops below a certain threshold (or some other measured event occurs), the system is adapted to allow additional compressed gas to be released from the reservoir. This ensures that the implant maintains a desired pressure and thus tissue is expanded as expected.

In some embodiments the system has preset limitations to prevent the user from using the system in certain ways. For example, as set forth in at least U.S. application. Ser. No. 12/973,693, filed Dec. 20, 2010, the system can be adapted to prevent the patient from releasing too much compressed gas without a given period of time. The system can also be adapted to prevent the release or more than a given total amount of gas from the reservoir. In some embodiments the system is adapted so that the preset limitations can be overridden. For example, a physician can use the master key to reprogram the remote controller to override the preset parameters.

U.S. application Ser. No. 12/973,693 describes a system in which the release of gas from the gas reservoir occurs when the valve in the valve assembly is opened in response to an electrical signal from the antenna (which responds to actuation of the remote controller). In some embodiments the dosing occurs (i.e., the valve is opened) is response to the application of a relatively strong external magnetic field. In some embodiments the physician or patient uses a magnet or electromagnet placed in proximity to the implant to open the valve and release gas. Application of the external magnetic field can be used intermittently in the same manner in which the remote dosage controller is actuated. The external magnetic field could be applied in situations where there is a communication failure between the implant and the remote controller without having to remove the implant from the patient.

In some situations a fluid such as a gas can become trapped between the inner anterior panel and the exterior shell. This can occur when gas permeates through the anterior panel. In some embodiments the exterior shell, such as an elastic exterior shell, has one or more apertures through it that prevent air from being trapped.

Holes can also be made in the external shell to allow perfusion of fluid there through. For example, holes can be used in drug delivery methods to deliver chemotherapeutic agent, antibiotics, etc., to site specific locations. For example, nearly all chemotherapeutic agents have a low therapeutic index. Due to the limited efficacy of most chemotherapeutic agents against the majority of solid tumors, it is desirable to increase the concentration and total dose of drug to the tumor bed than can be safely achieved by a systemic infusion. The space between the inner bag and outer shell provides an ideal location to place a bolus of chemotherapeutic agent intended for regional chemotherapy. A chemotherapeutic agent is locally dispersed through the vent holes in the outer shell.

In some embodiments a dedicated fluid agent reservoir is disposed between the anterior panel and the exterior shell. After implantation, the fluid agent is locally dispersed through vent holes in the outer shell.

In some embodiments the outer shell and/or inner layers are coated or impregnated with an antimicrobial or multiple substances. For devices in which the outer shell is not a fluid barrier, it can be constructed to provide antimicrobial or other therapeutic benefit.

In some of the embodiments herein there is a single remote dosage controller that is synched up with a single implant. In some embodiment, however, a single remote dosage controller is adapted to control a plurality of implants. Each of the implants can be implanted in different patients, or multiple implants can be implanted in a single patient. Each of the implants can have its own preset parameters or the implants can have the same preset parameters. The remote controller is adapted to store the parameters for each of the implants.

In some embodiments the system is adapted to provide one or more indications to the patient or other user, such as a physician. The indications convey one or more types of information to the physician and/or patient. The remote dosage controller or other remote device is adapted to provide the information. In some embodiments the information is communicated to the user via an interface on the remote dosage controller. The interface can include any number of known outputs to communicate the information. For example, the remote dosage controller can have an LCD screen that indicates one or more type of information about the system. In other embodiments a plurality of LED can be used to provide information to the user.

In some embodiment the system includes an indicator that communicates to a user the level of inflation of the inflatable chamber. The indicator can communicate the pressure in the inflatable chamber, how much gas has been released from the gas reservoir, or provide an indication of how full the inflatable chamber is as a percentage of a maximum level of inflation. For example, an LCD screen could indicate with icons or bars the level of inflation. The indicator could also be a numerical indication, indicating a pressure, volume of gas released, or percent full.

In some embodiments the indicator communicates the amount of gas remaining in the gas reservoir. For example, the remote dosage controller can include a screen with a number of bars that indicate how much gas remains, similar to a battery life indicator on a smartphone.

In some embodiments the indicator communicates information indicative of the most recent dose, or a time history of doses. For example, the indicator can communicate when or how much gas was released in the most recent dose. The indicator can be a numerical indicator on a LCD screen that provides a time, for example, of the most recent dose.

In some embodiments the system includes an indicator that provides an alert to the user. The remote controller, or a handheld device like a smartphone that is in communication with system, can have the indicator that is adapted to provide an alert. The alert can be a reminder alert that reminds the user to administer a dose. For example, if a certain period of time has passed without dosing, the system is adapted to generate an alert, such as a visual alert (e.g., blinking LED, icon flashing on an LCD screen), audio alert (e.g., beeping sound), or a tactile alert (e.g., vibration) to the user. The alert can occur on the remote dosage controller, such as an illuminated LED or a beep generated by an audio system. In some embodiments the remote dosage controller sends an output to a remote device such as a smartphone when an event has triggered the alert. The handheld device can provide the alert to the user. For example, the smartphone can vibrate or emit a certain ringtone to communicate the alert to the user. Any number of suitable alerts can be communicated to a user in this manner. Other indicators can be provided with the alert. For example, if there is an alert that dosing has not occurred for a given period of time, the alert can be accompanied with a visual indication (e.g., numerals) of when the last dosage occurred.

The remote dosage controller (or other remote device) can include an interface that allows the user to interact with the device. For example, the remote controller can include a touchscreen or buttons that allows the user to access information indicative of the system. As an example, the user can view a listing of the times of previous doses by accessing this information via the interface.

The system interface can also be adapted to allow the user (e.g., patient) to send a request to a physician to review and/or modify the system parameters remotely. For example, if a patient notices excessive permeation and the patient wishes that the physician override the system parameters to allow more gas to be released that would be allowed under the preset parameters, the patient can actuate the remote dosage controller (or other remote device) to send a notification to the physician. This can prompt the physician to review the status of the implant (e.g., percent full, the amount of gas released, internal pressure, etc.) and perhaps other patient information to determine if the parameters can be overridden or if there should be an office visit. The physician can then remotely send a communication to the remote controller that changes, by overriding, one or more parameters of the system.

The systems described herein and in the applications incorporated by reference use very little energy to release the gas from the gas reservoir into the inflatable chamber. One advantage of this is that batteries are not required onboard the implant. Less than 20 milliwatts are used during dosing. The remote dosage controller includes batteries to power the operation.

In some embodiments the implant includes one or more internal sensors to sense or more implant conditions. For example, the implant can include a pressure sensor that senses internal pressure within the inflatable chamber. This can provide an indication of how much expansion has taken place within the implant. In these embodiments the remote dosage controller can include an interface that provides an indication of the internal pressure. The status of the internal pressure can be used in combination with the alerts provided herein.

In some embodiments the system includes a proximity sensor that can be used to detect the proximity of a target on the implant and a sensor in the remote dosage controller. The target can be on the anterior portion of the implant, such as on the anterior panel or on the communication component. The sensor detects the proximity of the target, which provides an indication of how much expansion of the chamber has occurred.

The systems described herein and in the applications incorporated by reference are advantageous to previous attempts in that there is substantially less pain (if any) associated with the tissue expansion. One of the factors that provides this benefit is that the systems herein expand the inflatable chamber on more continuous basis than previous attempts, which administer boluses of fluid. This allows for more gradual, step-wise, inflation, which reduces pain and discomfort. Another significant advantage of the relatively continuous expansion is that the time to full expansion is substantially less. The systems described herein can expand tissue and create a pocket in about 15 days, as opposed to previous attempts that can take as much as 6 weeks.

What is claimed is:

1. A tissue expander comprising:
an implantable portion comprising a fluid source in communication with an expandable chamber, wherein the expandable chamber includes an anterior portion, wherein the anterior portion includes a first deformable member and a second deformable member, wherein the first deformable member is disposed within the second deformable member, and the first deformable member has a thickness that is about 1.5 to about 8 times the thickness of the second deformable member.

2. The tissue expander of claim 1 wherein the first deformable member at least partially defines the expandable chamber.

3. The tissue expander of claim 2 wherein the second deformable member is configured as a barrier layer to the fluid.

4. The tissue expander of claim 1 further comprising an outer shell disposed at least partially around the first and second deformable members.

5. The tissue expander of claim 4 wherein the outer shell is an elastic shell.

6. The tissue expander of claim 1 wherein the first deformable member has a pre-formed configuration.

7. The tissue expander of claim 6 wherein the first deformable member comprises an inelastic material with the pre-formed configuration.

8. The tissue expander of claim 6 wherein the second deformable member has a pre-formed configuration.

9. The tissue expander of claim 8 wherein the first and second deformable members have pre-formed configurations that are substantially the same.

10. The tissue expander of claim 1 wherein the first and second deformable members are thin-walled deformable members.

11. The tissue expander of claim 10 wherein the first deformable member has a thickness between about 75 microns and about 150 microns.

12. The tissue expander of claim 11 wherein the second deformable member has a thickness between about 25 microns and about 75 microns.

13. The tissue expander of claim 10 wherein the second deformable member has a thickness between about 25 microns and about 75 microns.

14. A tissue expander comprising:
an implantable portion comprising a fluid source in communication with an expandable chamber, wherein the expandable chamber includes an anterior portion, wherein the anterior portion includes a first deformable member and a second deformable member, wherein the first deformable member is disposed within the second deformable member, and the first deformable member has a thickness between about 75 microns and about 150 microns.

15. The tissue expander of claim 1 wherein at least one of the first and second deformable members comprises multiple layers of material secured together.

16. The tissue expander of claim 1, further comprising a lubricious material disposed between the first and second deformable members to reduce friction between the first and second deformable members, wherein the lubricious material has a viscosity of at least 50 cP.

17. The tissue expander of claim 16 wherein the lubricious material is a biocompatible lubricant.

18. The tissue expander of claim 17 wherein the biocompatible lubricant is a silicone-based lubricant.

19. The tissue expander of claim 1 wherein the first deformable members is attached directly to the second deformable member.

20. The tissue expander of claim 19 wherein the first and second deformable members are secured to each other at respective peripheries of the first and second deformable members.

21. The tissue expander of claim 1 wherein the expandable chamber includes a posterior backing coupled to the first deformable member.

22. The tissue expander of claim 1 wherein the first deformable member has a communication component secured to it, wherein the communication component is configured for wireless communication with an external controller.

23. The tissue expander of claim 16 wherein the volume of lubricious material disposed between the first and second members is between about 0.5 mL and about 2.5 mL.

24. The tissue expander of claim 23 wherein the volume of lubricious material disposed between the first and second members is between about 0.5 mL and about 2.0 mL.

25. The tissue expander of claim 1 further comprising an external controller adapted to be in communication with the implantable portion to enable fluid to be released from the fluid source into the expandable chamber.

26. The tissue expander of claim 16 wherein the lubricious material comprises a coating on at least one of the two members.

27. The tissue expander of claim 16 wherein the lubricous material provides substantially no additional thickness to the implantable portion.

28. A tissue expander comprising:
an implantable portion including
an expandable chamber in fluid communication with a fluid source;
a first deformable member at least partially defining the expandable chamber and having a pre-formed configuration;
a second deformable member disposed about the first deformable member, wherein the second deformable member has a pre-formed configuration; and
an outer elastic shell disposed about the first and second deformable members.

29. The tissue expander of claim 28 wherein the first and second pre-formed configurations are substantially the same.

30. The tissue expander of claim 28 wherein the first and second deformable members form at least part of a gas barrier layer of the implantable portion that is substantially impermeable to fluid in the fluid source.

31. The tissue expander of claim 28 wherein the first and second deformable members are thin-walled deformable members.

32. The tissue expander of claim 28 wherein the first deformable member is disposed inside the second deformable member, and the first deformable member has a thickness between about 75 microns and about 150 microns.

33. The tissue expander of claim 32 wherein the second deformable member has a thickness between about 25 microns and about 75 microns.

34. The tissue expander of claim 28 wherein the first deformable member is disposed inside the second deformable member, and the second deformable member has a thickness between about 25 microns and about 75 microns.

35. The tissue expander of claim 28 wherein the first deformable member is disposed inside the second deformable member, and the first deformable member has a thickness that is about 1.5 to about 8 times the thickness of the second deformable member.

36. A tissue expander comprising:
an implantable portion comprising a fluid source in fluid communication with an expandable chamber, a communication element secured to the expandable chamber and movable relative to the expandable chamber, wherein the communication element is disposed inside a pocket, and the pocket is attached to the expandable chamber, and wherein the communication element is secured inside the pocket such that it floats inside the pocket.

37. The tissue expander of claim 36 wherein the communication element is an antenna.

38. The tissue expander of claim 36 wherein the communication element is stiffer than the expandable chamber.

39. The tissue expander of claim 36 wherein the expandable chamber has a thickness between about 50 microns and about 150 microns.

40. The tissue expander of claim 36 wherein two side of the pocket are attached together at a plurality of discrete locations with at least one unattached location between the two sides.

41. A tissue expander comprising:
an implantable portion comprising a fluid source in fluid communication with an expandable chamber, a communication element secured to the expandable chamber and movable relative to the expandable chamber, wherein the communication element is disposed inside a pocket, and wherein the pocket is attached to the expandable chamber at a plurality of discrete locations with at least one unattached location where the pocket is not attached to the expandable chamber.

42. The tissue expander of claim 41 wherein the pocket is secured to the expandable chamber around a periphery of the pocket at at least three locations with unsecured locations where the pocket is not attached to the expandable chamber.

43. The tissue expander of claim 36 wherein the communication element is secured to a first portion of the expandable chamber that, in a side view of an expanded configuration of the expandable chamber, is less curved than a second portion of the expandable chamber.

44. The tissue expander of claim 36 wherein the expandable chamber comprises an inelastic material with a preformed expanded configuration, and the communication element is secured to the inelastic material such that it can move relative to the inelastic material.

* * * * *